(12) United States Patent
Piferi et al.

(10) Patent No.: US 11,253,333 B2
(45) Date of Patent: Feb. 22, 2022

(54) DEVICES FOR SURGICAL NAVIGATION SYSTEMS

(71) Applicant: ClearPoint Neuro, Inc., Irvine, CA (US)

(72) Inventors: Peter G. Piferi, Orange, CA (US); Jesse Flores, Perris, CA (US); Maxwell Jerad Daly, Redlands, CA (US); Rajesh Pandey, Irvine, CA (US)

(73) Assignee: ClearPoint Neuro, Inc., Irvine, CA (US)

( * ) Notice: Subject to any disclaimer, the term of this patent is extended or adjusted under 35 U.S.C. 154(b) by 287 days.

(21) Appl. No.: 16/454,322

(22) Filed: Jun. 27, 2019

(65) Prior Publication Data

US 2019/0314110 A1    Oct. 17, 2019

Related U.S. Application Data

(62) Division of application No. 15/348,310, filed on Nov. 10, 2016, now Pat. No. 10,376,333.

(60) Provisional application No. 62/278,760, filed on Jan. 14, 2016.

(51) Int. Cl.
| | |
|---|---|
| *A61B 90/11* | (2016.01) |
| *A61B 34/00* | (2016.01) |
| *A61B 34/20* | (2016.01) |
| *A61B 90/10* | (2016.01) |
| *A61B 90/00* | (2016.01) |

(52) U.S. Cl.
CPC ............. *A61B 90/11* (2016.02); *A61B 34/72* (2016.02); *A61B 2034/2057* (2016.02); *A61B 2034/2072* (2016.02); *A61B 2090/103* (2016.02); *A61B 2090/3983* (2016.02)

(58) Field of Classification Search
CPC ......... A61B 90/00; A61B 90/10; A61B 90/11; A61B 19/201; A61B 19/203; A61B 19/5244; A61B 34/00; A61B 34/20; A61B 34/72; A61B 2034/2057; A61B 2034/2072
See application file for complete search history.

(56) References Cited

U.S. PATENT DOCUMENTS

| | | |
|---|---|---|
| D216,458 S | 1/1970 | Nestrock |
| D251,017 S | 2/1979 | Amezcua |
| D261,175 S | 10/1981 | O'Day |
| D266,142 S | 9/1982 | Sikstrom |
| D292,021 S | 9/1987 | Stoll |
| 4,819,521 A | 4/1989 | Lang |

(Continued)

OTHER PUBLICATIONS

Brainlab Airo® Mobile Intraoperative CT, Brochure, 10 pages (2014).

(Continued)

*Primary Examiner* — Vi X Nguyen
(74) *Attorney, Agent, or Firm* — Myers Bigel, P.A.

(57) ABSTRACT

Trajectory frame assemblies for image guided surgical systems have a trajectory frame with a support column that can removably secure different components such as a tracking probe and an MER driver adapter to define and/or follow a desired intrabody trajectory. The trajectory frame assemblies include fins attached to the column support and a platform optionally with an X-Y table and/or arcuate reference brackets that are attached to the trajectory frame assemblies and can hold a reference frame with fiducials.

6 Claims, 24 Drawing Sheets

(56) References Cited

U.S. PATENT DOCUMENTS

| | | | |
|---|---|---|---|
| D306,577 S | 3/1990 | Matsutani et al. | |
| 5,116,345 A | 5/1992 | Jewell et al. | |
| D330,154 S | 10/1992 | Wagner | |
| D356,460 S | 3/1995 | Vogels | |
| 5,507,742 A | 4/1996 | Long et al. | |
| 5,582,488 A | 12/1996 | Dudley et al. | |
| 5,592,939 A | 1/1997 | Martinelli et al. | |
| D378,133 S | 2/1997 | Murakami et al. | |
| D378,233 S | 2/1997 | Warner | |
| 5,913,820 A | 6/1999 | Bladen et al. | |
| 6,050,992 A | 4/2000 | Nichols | |
| 6,167,311 A | 12/2000 | Rezai | |
| D439,498 S | 3/2001 | Hennig | |
| D444,233 S | 6/2001 | Bohanan | |
| D453,143 S | 1/2002 | Jones | |
| 6,356,786 B1 | 3/2002 | Rezai et al. | |
| 6,405,079 B1 | 6/2002 | Ansarinia | |
| 6,438,423 B1 | 8/2002 | Rezai et al. | |
| 6,526,318 B1 | 2/2003 | Ansarinia | |
| 6,539,263 B1 | 3/2003 | Schiff et al. | |
| D472,970 S | 4/2003 | Lund | |
| 6,609,030 B1 | 8/2003 | Rezai et al. | |
| 6,675,037 B1 | 1/2004 | Tsekos | |
| 6,708,064 B2 | 3/2004 | Rezai | |
| D490,698 S | 6/2004 | Graves et al. | |
| 6,799,074 B1 | 9/2004 | Thomas et al. | |
| 6,920,347 B2 | 7/2005 | Simon et al. | |
| 6,940,941 B2 | 9/2005 | Gregerson et al. | |
| 6,949,106 B2 | 9/2005 | Brock et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,219,665 B1 | 5/2007 | Braithwaite | |
| 7,491,198 B2 | 2/2009 | Kockro | |
| 7,658,879 B2 | 2/2010 | Solar | |
| 7,706,600 B2 | 4/2010 | Kreeger et al. | |
| 7,720,522 B2 | 5/2010 | Solar et al. | |
| 7,730,563 B1 | 6/2010 | Sklar et al. | |
| 7,751,865 B2 | 7/2010 | Jascob et al. | |
| D621,244 S | 8/2010 | Kundinger, Jr. et al. | |
| 8,073,530 B2 | 12/2011 | Solar et al. | |
| 8,150,494 B2 | 4/2012 | Simon et al. | |
| 8,175,677 B2 | 5/2012 | Sayler et al. | |
| 8,195,272 B2 | 6/2012 | Piferi et al. | |
| 8,238,631 B2 | 8/2012 | Hartmann et al. | |
| 8,315,689 B2 | 11/2012 | Jenkins et al. | |
| 8,340,743 B2 | 12/2012 | Jenkins et al. | |
| 8,374,677 B2 | 2/2013 | Piferi et al. | |
| 8,543,189 B2 | 9/2013 | Paitel et al. | |
| D699,544 S | 2/2014 | Lin | |
| D713,031 S | 9/2014 | McCormick | |
| D737,965 S | 9/2015 | Bende | |
| 9,192,446 B2 | 11/2015 | Piferi et al. | |
| D751,699 S | 3/2016 | Mills | |
| 9,387,010 B2 | 7/2016 | Mark et al. | |
| D772,041 S | 11/2016 | Miner et al. | |
| D789,541 S | 6/2017 | Brunst | |
| 9,694,158 B2 | 7/2017 | Slim | |
| 9,857,733 B2 | 1/2018 | Matsuzaki et al. | |
| D824,027 S | 7/2018 | Flores et al. | |
| D829,904 S | 10/2018 | Piferi et al. | |
| D831,824 S | 10/2018 | Antalffy | |
| D832,436 S | 10/2018 | Loewe | |
| 10,307,220 B2* | 6/2019 | Piferi | A61N 1/372 |
| 2001/0018584 A1 | 8/2001 | Bays | |
| 2003/0181810 A1 | 9/2003 | Murphy et al. | |
| 2004/0075768 A1 | 4/2004 | Law et al. | |
| 2004/0215071 A1 | 10/2004 | Frank et al. | |
| 2005/0242055 A1 | 11/2005 | Oh | |
| 2006/0053922 A1 | 3/2006 | Laabs | |
| 2006/0282044 A1 | 12/2006 | Mohammed | |
| 2007/0129629 A1 | 6/2007 | Beauregard et al. | |
| 2007/0221218 A1 | 9/2007 | Warden et al. | |
| 2008/0097193 A1 | 4/2008 | Karmarkar | |
| 2008/0214922 A1 | 9/2008 | Hartmann et al. | |
| 2008/0275466 A1 | 11/2008 | Skakoon | |
| 2009/0112084 A1* | 4/2009 | Piferi | A61B 5/0036 600/421 |
| 2010/0125240 A1 | 5/2010 | Spedden et al. | |
| 2010/0229414 A1 | 9/2010 | Nonni et al. | |
| 2011/0083672 A1 | 4/2011 | Webster et al. | |
| 2011/0152860 A1 | 6/2011 | Morejohn et al. | |
| 2012/0046542 A1 | 2/2012 | Csavoy et al. | |
| 2012/0330135 A1 | 12/2012 | Millahn et al. | |
| 2013/0060146 A1 | 3/2013 | Yang et al. | |
| 2013/0072940 A1 | 3/2013 | Dawood et al. | |
| 2015/0031982 A1 | 1/2015 | Piferi et al. | |
| 2016/0324592 A1 | 11/2016 | Schuele | |
| 2020/0246101 A1 | 8/2020 | Jones et al. | |

OTHER PUBLICATIONS

Brainlab Buzz™ Digital O.R., Brochure, 12 pages (2012).
Brainlab Curve™ Image Guided Surgery, Brochure, 18 pages (2012).
Brainlab, Dash® Digital Cutting Block Alignment Tool, 1 page, Published on Apr. 24, 2014 at URL https://www.youtube.com/watch?v=9Q8iOXVW2P0.
Brainlab, Image-Guided Surgery Platforms, 2 Pages, Retrieved from the internet on Oct. 1, 2014 at URL https://www.brainlab.com/surgery-products/overview-platform-products/.
Brainlab Kick® Purely Navigation Using Optical Tracking, 4 pages, Retrieved from the internet on Jan. 16, 2015 at URL https://www.brainlab.com/en/surgery-products/overview-platform-products/kick-navigation/.
Image Guided Surgery for Brain Tumors, Published on Feb. 26, 2013 at URL http://www.youtube.com/watch?v=tJTR4ty0BW4.
Medtronic, Deep Brain Stimulation for Movement Disorders, 2 Pages, Retrieved from the internet on Sep. 22, 2014 at URL http://professional.medtronic.com/pt/neuro/dbs-md/prod/procedure-solutions/index.htm.
Medtronic Framelink™, Simplified Planning and Navigation for DBS Procedures, 2 pages (2009).
Medtronic Nexframe Stereotactic Image Guided System, 2 pages, Retrieved from the internet on Jan. 16, 2015 at URL http://professional.medtronic.com/pt/neuro/dbs-md/prod/procedure-solutions/features-specifications/#.VLk0N9LF To.
Medtronic Stealth Station® Surgical Navigation Systems, Dec. 11, 2014, 2 pages, Retrieved from the internet at URL http://www.medtronic.com/for-healthcare-professionals/products-therapies/spinal/surgical-navigation-imaging/surgical-navigation-systems/.
MRI Interventions, Inc. "ClearPoint Demonstration Video" https://www.YouTube.com/watch?v=IA45R kvBR8 (1 page) (announced Sep. 15, 2015) (site visited Mar. 16, 2018).
Northern Digital Inc., NDI, Disposable Reflective Marker Spheres for Brainlab IGS Systems, 4 pages, Retrieved from the internet on Jan. 16, 2015 at URL http://spheres.ndigital.com/.
Northern Digital Inc., The Original IGS Sphere, 7 Pages, Retrieved from the internet on Sep. 22, 2014 at URL http://spheres.ndigital.com/ndi-passive-spheres/.
Photographs obtained of commercial probe tracking devices, date photographs on internet first available unknown, but prior to filing the pending application on Oct. 15, 2014, 1 page.
Stryker eNlite Navigation System, 1 page, Retrieved from the internet on Jan. 16, 2015 from URL http://www.stryker.com/latm/products/OREquipmentConnectivity/SurgicalNavigation/SurgicalNavigationSystems/EnliteLaptop/index.htm.
Stryker Integrated NavSuite Operating Room, 2008, Brochure, 3 pages.
Stryker System II Navigation System, 2006, Brochure, 2 pages.

* cited by examiner

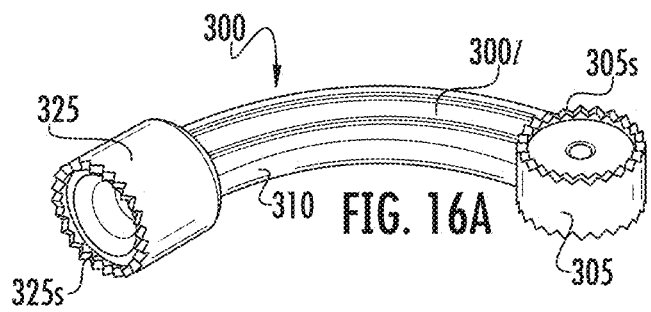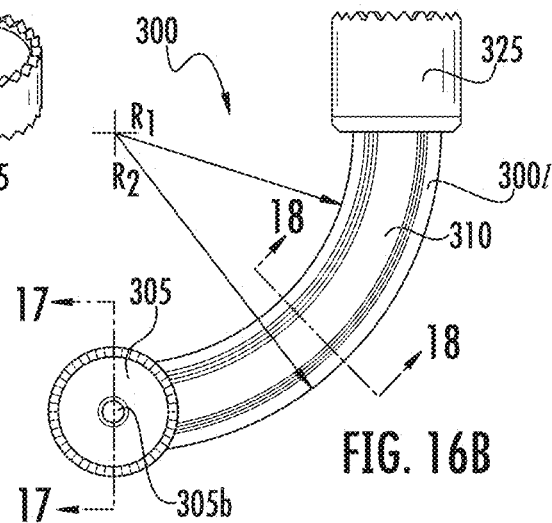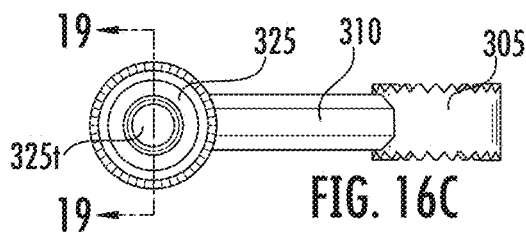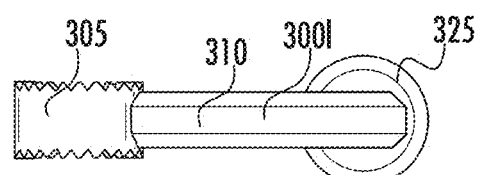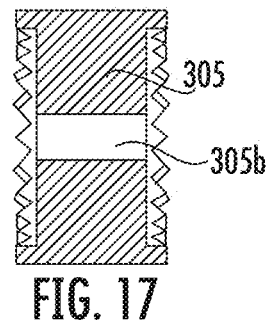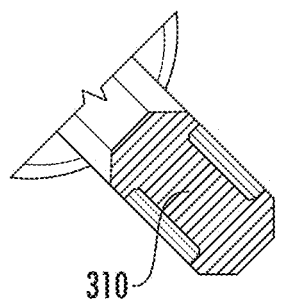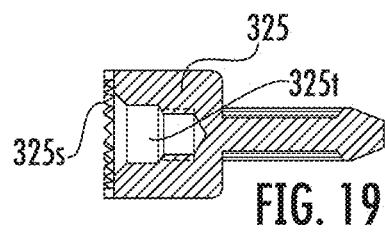

DEVICES FOR SURGICAL NAVIGATION SYSTEMS

RELATED APPLICATIONS

This application is a divisional application of U.S. patent application Ser. No. 15/348,310, filed Nov. 10, 2016, which claims the benefit of and priority to U.S. Provisional Application Ser. No. 62/278,760, filed Jan. 14, 2016, the contents of which are hereby incorporated by reference as if recited in full herein.

FIELD OF THE INVENTION

The present invention relates to surgical navigation systems or tools for placement/localization of interventional medical devices and/or therapies in the body.

BACKGROUND OF THE INVENTION

Conventional, so-called image guided systems (IGS), also referred to as surgical navigation systems, are becoming more common and widely adapted in surgeries including neurosurgery. Examples include, for example, navigation systems that use electromagnetic sensors or cameras with optical fiducials for tracking and registering tools and patients from an imaging space to a surgical space. Currently, many IGS systems are based on obtaining a preoperative series of imaging data, such as, e.g., MRI and CT images which are registered to the patient in the physical world or surgical space and which include tracking systems for navigation during surgery. Optical tracking allows for detecting markers placed on a patient's skin and/or and surgical tools (known as "fiducials") using a camera for registration between an imaging space and a surgical space. Electromagnetic ("EM") tracking systems are also used for surgical navigation. See, e.g., U.S. Pat. Nos. 7,706,600; 7,491,198; and 8,238,631 and US Patent Application Publications 2004/075768; 2012/0330135; and 2013/0060146, the contents of which are hereby incorporated by reference as if recited in full herein.

SUMMARY OF EMBODIMENTS OF THE INVENTION

Embodiments of the present invention are directed to devices and assemblies that can work with one or more imaging modalities to facilitate surgical procedures.

Some embodiments are directed to trajectory frames configured to employ optical and/or EM fiducials for tracking/navigation without requiring MRI imaging.

The navigation systems or devices may be used with MRI-guided navigation systems, camera-based and/or EM-based tracking and/or navigation systems.

Some embodiments are directed to trajectory frames and/or devices attached thereto configured to hold or employ CT visible image fiducials for non-MRI imaging modalities.

Some embodiments of the present invention are directed to navigation systems that can provide information that can be used to confirm that a planned trajectory using an optical or EM tracking/position system is correct to reduce radiation, increase the speed and/or reliability of an intrabody procedure.

Embodiments of the invention provide surgical devices with fiducials that can be electronically identified in images generated using one or more imaging modalities such as, for example, CT, X-ray, PET and the like.

In some embodiments, the tools/devices with the fiducials can be hybrid tools/devices that can be used for more than one imaging modality, e.g., MRI and CT. The fiducials can comprise a fiducial material that can be CT-visible fluid and an MRI-visible fluid that creates sufficient signal intensity for identifying a location and/or orientation of a target tool.

Some embodiments are directed to a trajectory frame for use with a surgical system. The trajectory frame can have a base having a patient access aperture formed therein. The base can be configured to be secured to a body of a patient. The trajectory frame can also include a yoke movably mounted to the base and rotatable about a roll axis, a platform movably mounted to the yoke and rotatable about a pitch axis, and an elongated support column secured to the platform. The support column includes opposite proximal and distal end portions. The distal end portion can be positioned proximate the patient access aperture. The support column can include a bore therethrough that extends from the proximal end portion to the distal end portion. The support column guide can be configured to releasably secure at least one device within the bore. The support column can include a plurality of circumferentially spaced apart and radially outwardly extending fins that extend from an external wall thereof.

The at least one device that is received within the bore can be or include an elongate tracking probe mount holding a tracking probe with reflective members arranged in a fixed geometric relationship relative to each other. The reflective members can be configured to be detectable by a camera-based tracking system.

The at least one device can further include a microelectric probe driver adapter. The proximal end portion of the guide can be configured to serially, interchangeably and removably secure the tracking probe mount and the microelectrode probe drive adapter.

The trajectory frame can include a bracket attached thereto that has a curved arm that extends outward therefrom and holds a reference frame that has a plurality of spaced apart reflective fiducials in a fixed geometry.

The platform can include an X-Y support table movably mounted to the platform that is configured to move in an X-direction and Y-direction relative to the platform. The support column can be attached to the X-Y support table and the fins of the support column can be attached to an upper surface of the X-Y support table.

The trajectory frame can include a plurality of spaced apart ears held by and extending laterally outward away from the base, the ears can have upper and lower surfaces and a bracket with a first upright segment residing under and attached to one ear supporting a curved arm that extends outwardly therefrom. The curved arm can hold a starburst connector on an end portion of the arm configured to engage a reference frame with an array of optical fiducials thereon for tracking by a camera based tracking system.

The bracket starburst connector can have a first swivel axis that allows positional adjustment of an end portion of the arm. The first upright segment can have a starburst connector that has a second swivel axis that is orthogonal to the first swivel axis.

The base can be configured to be secured to the scalp or skull of a patient about a burr hole formed therein.

The guide bore can be configured to guide intra-brain placement of at least one device in vivo. The trajectory frame can include a bracket attached thereto that has a curved arm that extends therefrom and holds a reference frame with a plurality of spaced apart reflective members that are configured to be detectable by a camera.

These and other embodiments will be described further below. It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

FIG. 16A is a side perspective view of a "short" reference bracket according to embodiments of the present invention.

FIG. 16B is a top view of the bracket shown in FIG. 16A.

FIG. 16C is a side view of the bracket shown in FIG. 16A.

FIG. 16D is an opposing side view thereof.

FIG. 17 is an enlarged section view taken along line 17-17 in FIG. 16B.

FIG. 18 is an enlarged section view taken along line 18-18 in FIG. 16B.

FIG. 19 is an enlarged section view taken along line 19-19 in FIG. 16C.

DETAILED DESCRIPTION OF EMBODIMENTS OF THE INVENTION

Figure 1:
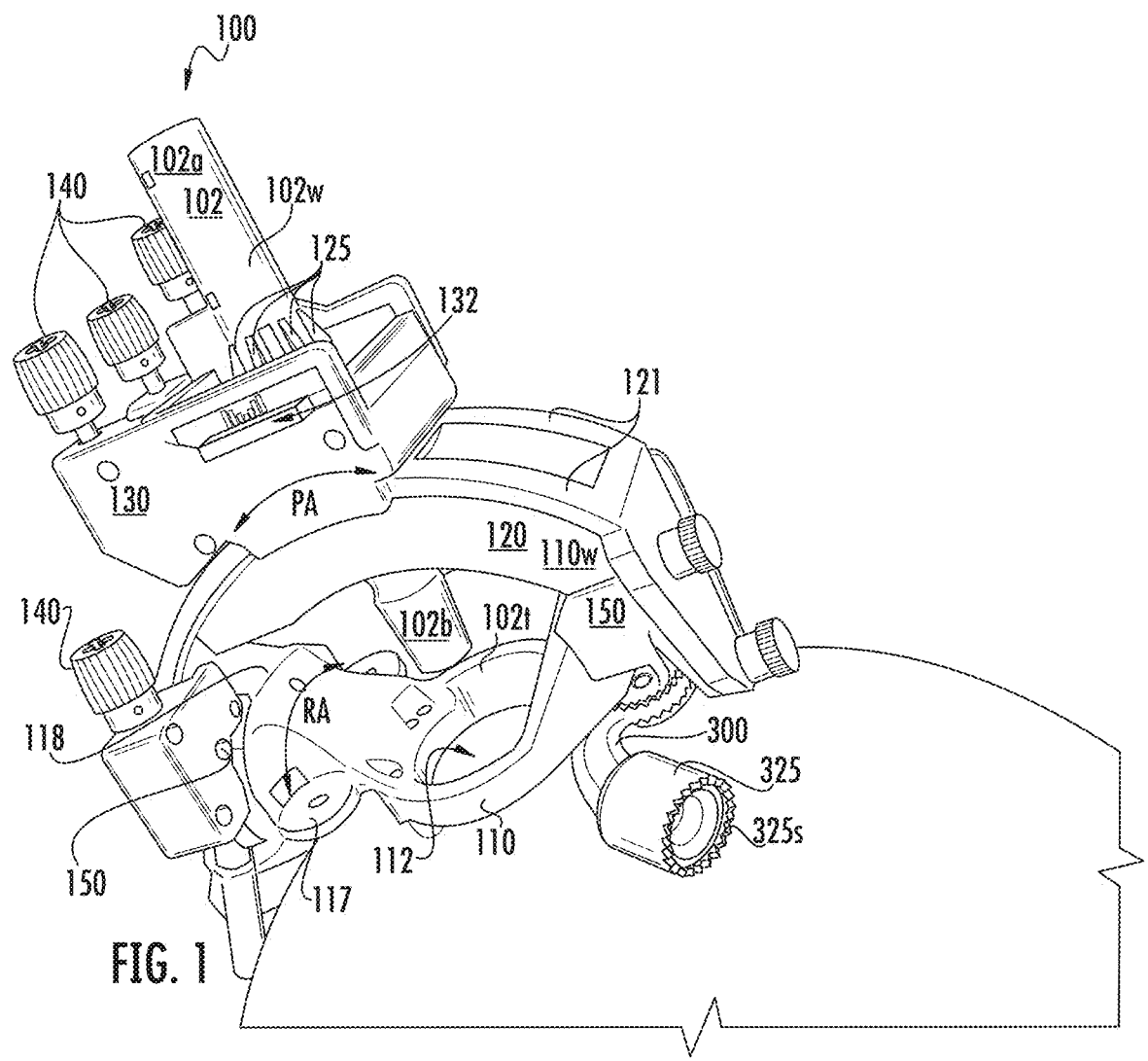
FIG. 1 is a side perspective view of a trajectory frame assembly for an image-guided surgical system according to some embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit of flow diagrams) illustrate optional features or operations, unless specified otherwise. In addition, the sequence of operations (or steps) is not limited to the order presented in the claims unless specifically indicated otherwise. The abbreviations "Fig." and "FIG." are used interchangeably with the word "Figure" to refer to the drawings.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

Visualizations can be shown on a screen or display so that the map and/or anatomical or tool structure is in a flat 2-D view and/or in 2-D what appears to be 3-D volumetric images with data representing features or electrical output with different visual characteristics such as with differing intensity, opacity, color, texture and the like. A 4-D map illustrates time-dependent activity, such as electrical activity or blood flow movement.

The term "ACPC coordinate space" refers to a right-handed coordinate system defined by anterior and posterior commissures (AC, PC) and Mid-Sagittal plane points, with positive directions corresponding to a patient's anatomical Right, Anterior and Head directions with origin at the mid-commissure point.

The term "fiducial marker" is used interchangeably with the term "fiducial" and refers to a marker that can be electronically identified using a detector, image recognition and/or electronic interrogation of image data for tracking position of a device in a surgical environment. The fiducial marker can be provided in any suitable manner, such as, but not limited to, a geometric shape of a portion of the tool, one or more components held by, on or in the tool, an electromagnetic tracking member (e.g., sensor or detector having a coil or coil array), a coating or fluid-filled component or feature (or combinations of different types of fiducial markers) that makes the fiducial marker(s) visible to a camera and/or in image data of a target imaging modality so that the image data has sufficient signal intensity (brightness) for identifying location and/or orientation information for the tool and/or components thereof in space. The fiducial markers or tracking members can include electromagnetic markers/members or passive optical markers, for example.

The term "visible" with respect to an image means that the device, feature or component, is visible, directly or indirectly, in an image. The visibility may be indicated by the increased SNR of the signal proximate the fiducial marker relative to an adjacent location without such fiducial marker.

The term "MRI compatible" means that the so-called component(s) is safe for use in an MRI environment and as such is typically made of a non-ferromagnetic MRI compatible material(s) suitable to reside and/or operate in a high magnetic field environment. The term "high-magnetic field" refers to field strengths above about 0.5 T, typically above 1.0T, and more typically between about 1.5T and 10T. MRI Scanners are well known and include high-field closed bore and open bore systems.

Embodiments of the present invention can be configured to carry out diagnostic and interventional procedures such as to guide and/or place interventional devices to any desired internal region of the body or object, but may be particularly suitable for neurosurgeries. The object can be any object, and may be particularly suitable for animal and/or human subjects. For example, the navigation system 10 can be used for drug delivery, stimulation lead (electrode) placement, gene and/or stem-cell based therapy delivery or other neural therapy delivery and allow user-defined custom targets in the brain or to other locations. In addition, embodiments of the systems can be used to ablate tissue in the brain or at other locations.

Examples of known treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

The term "image guided system" is used generally to refer to surgical navigation systems that include patient images (which may be acquired before a surgery and/or at defined points during a surgery to confirm location) but does not require a continuous series of images during the surgery.

Embodiments of the present invention will now be described in further detail below with reference to the figures. FIG. 1 illustrates an exemplary trajectory frame assembly 100. The trajectory frame assembly 100 includes a support column 102, a platform 130 and typically an X-Y table held by the platform 130. The support column 102 can be held by the platform 130 so that a proximal end 102*a* resides above the platform and a distal end 102*b* resides below the platform 130 and above the patient access aperture 112 formed by the base 110. The base 110 can attach to the skull of a patient as shown or other target objects or positions. The platform 130 can be attached to a yoke 120. The yoke 120 can be attached to arcuate arms 150 that extend up from the lower end of the base 110. At least one of the arcuate arms 150 can have an upper surface with a thread pattern 118 that can cooperate with a worm gear 186 (FIG. 3) in the yoke 120. Actuators 140 can be used to rotate the yoke 120 relative to the arm(s) 150, rotate the platform 130 relative to the yoke 120, and move the X-Y table 132 in X and Y directions.

The trajectory frame assembly 100 can provide X-Y adjustment and pitch and roll adjustment.

Referring to FIG. 1, the yoke 120 can have a pair of control arcs 121 that cooperate with the platform 130 to provide pitch and roll adjustments. The X-Y table 132 can allow for X-Y adjustments of the trajectory. The yoke 120 is rotatable about a roll axis RA (FIG. 1). The platform 130 is movably mounted to the yoke 120 and is rotatable about a pitch axis PA. The X-Y support table 132 can be configured to move in an X-direction (side to side) and Y-direction (front to back) relative to the platform 130.

Optionally, X-Y support table 132 may move in a Z-direction defined by the longitudinal axis of the column support 102. An X-direction actuator 140 is operably connected to the platform 130 and is configured to move the X-Y support table 132 in the X-direction. A Y-direction actuator 140 is operably connected to the platform 130 and is configured to move the X-Y support table 132 in the Y-direction. A pitch actuator 140 is operably connected to the platform 130 and is configured to rotate the platform 130 about the pitch axis PA. A roll actuator 140 communicates with the worm gear 186 (FIGS. 3, 5) and rotates the platform 132 about the roll axis RA.

The actuators 140 are configured to translate and/or rotate the frame.

When inserted within the guide 1102, a tracking probe 1160 (FIG. 6) or microelectrode driver adapter 1170 (FIG. 7A/7B) can help define and/or use a desired axial intrabody trajectory based on the position of the support column 102.

For further discussion of exemplary features of a trajectory frame and/or associated or cooperating components, see, e.g., U.S. Pat. Nos. 8,175,677, 8,340,743, and U.S. Patent Application Publication 2015/0031982, the contents of which are hereby incorporated by reference as if recited in full herein.

The trajectory frame assembly 100 can be used with surgical navigation systems in various imaging system modalities including, among other things, magnetic resonance imaging (MRI), computed tomography (CT), positron emission tomography (PET), and single photon emission computed tomography (SPECT) and fluoroscopic systems. In certain embodiments, the imaging modality is a radiation-based imaging modality such as CT. In some embodiments, the surgical navigation systems can be used in ultrasound and/or X-ray imaging modalities.

FIGS. 1 and 2 illustrate that the base 110 can have at least one laterally extending member 117, shown as a plurality of laterally extending members 117, typically with at least one planar surface. Where a plurality of laterally extending members 117 are used, they can be spaced apart about the perimeter of the patient access aperture 112 extending outward from the circular base wall 110*w* of the base 110 so as to not occlude the patient access aperture 112.

Figure 2A:
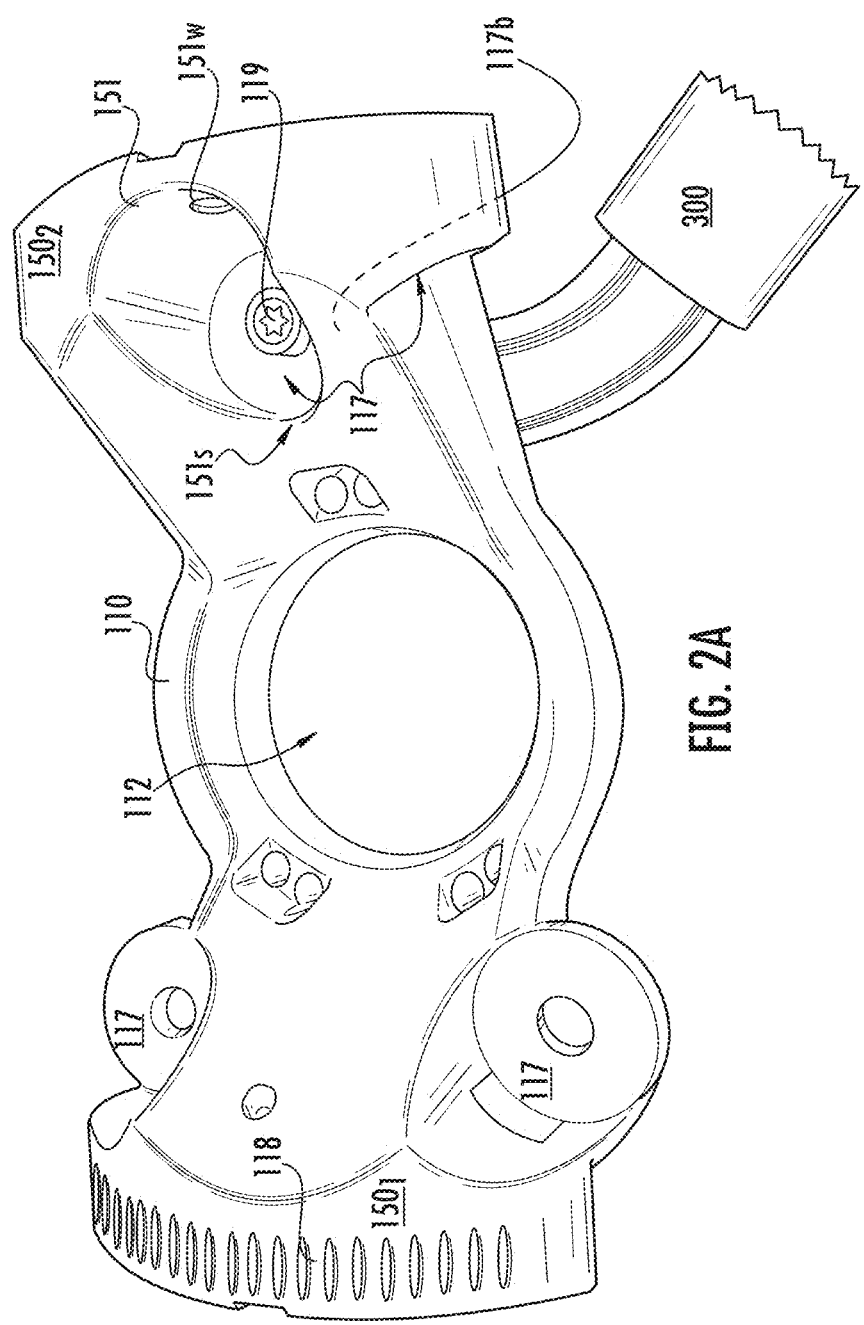
FIG. 2A is a top perspective view of a base of a trajectory frame assembly according to embodiments of the present invention.

As shown in FIG. 2A, two laterally extending members 117 can reside adjacent a first arcuate arm $150_1$ (under the yoke 120) and a single one can reside adjacent the second arcuate arm $150_2$ (also under the yoke 120). The second arm $150_2$ can have a recess 151 with a downwardly extending wall 151*w* that merges into the laterally extending member 117. The wall 151*w* can taper to have a shorter inwardly facing segment 151*s* relative to sides and an outer facing segment.

The laterally extending members 117 can be co-planar or may be parallel at different planes or heights, and/or have other relative configurations. The laterally extending members 117 can be arranged so that centers thereof are concentric and reside about a circle concentric with the circular patient access aperture 112 of the base 110.

In some embodiments, one laterally extending member 117 is aligned with the recess 151 and above a plane of a surface extending over the top of the wall 110*w* of the lower segment of the base 110 around the patient access aperture 112. The second arcuate arm $150_2$ can optionally be devoid of the thread pattern 118 on the other arm $150_1$.

Figure 2B:
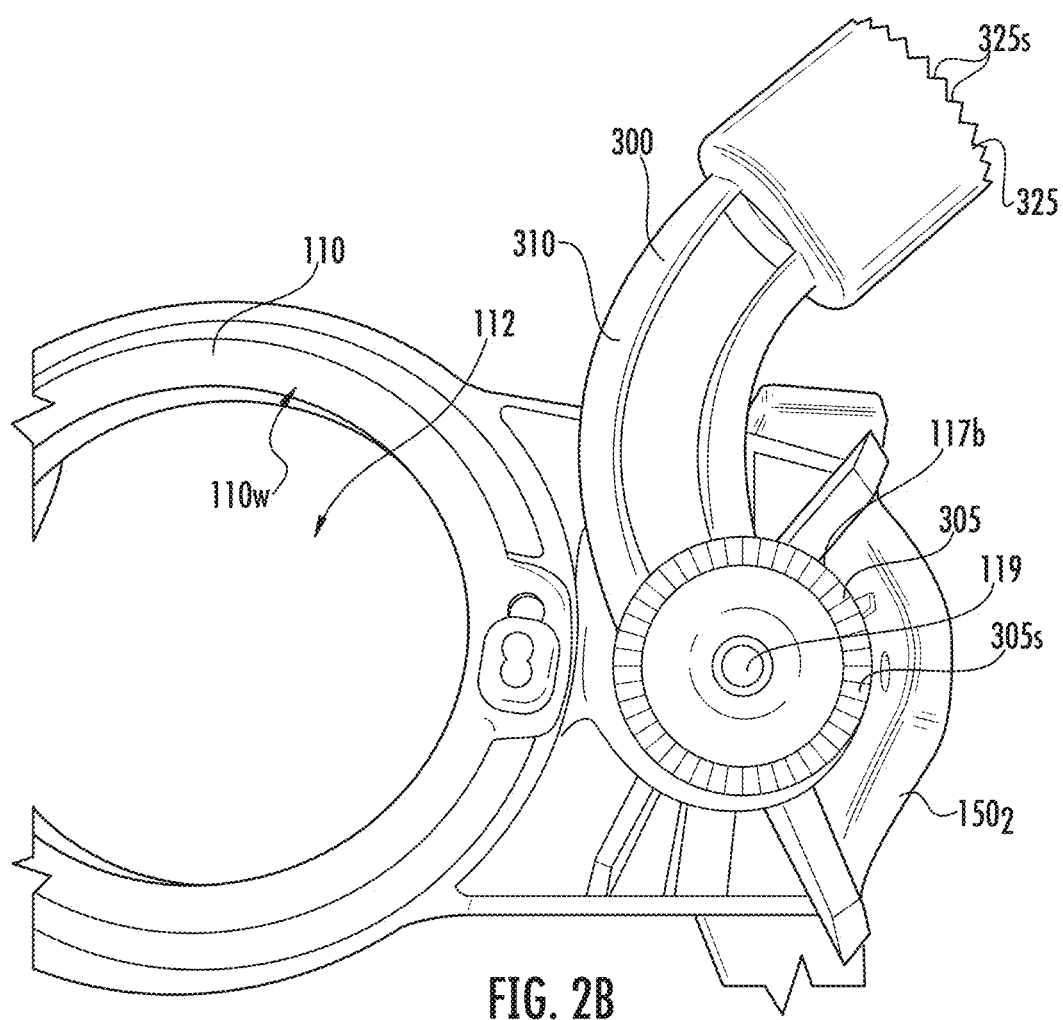
FIG. 2B is a bottom view of the base shown in FIG. 2A according to some embodiments of the present invention.

As shown in FIGS. 1, 2A and 2B, for example, the trajectory frame assembly 100 can hold at least one outwardly extending reference bracket 300. The bracket 300 can have a starburst connector 325 with a serrated perimeter 325*s* on an outer end thereof. The bracket 300 can have an opposing end 305 closer to the patient access aperture 112 that is attached to the base 110 of the trajectory frame assembly 110, typically to one of the laterally extending members 117.

As shown in FIGS. 1, 2A and 2B, the bracket 300 can be attached to a bottom surface 117*b* of the laterally extending member 117 that resides in the recess 151, typically under and within a perimeter of the arcuate arm $150_2$. The bracket 300 can be curved or arcuate with a radius of curvature and have a length sufficient to extend forward a distance outside of the perimeter of the base wall 110*w* as will be discussed further below. A fixation device 119 such as a pin, screw, nail or other attachment member can be used to affix the internal end 305 to the laterally extending member 117. The bracket 300 can have a starburst connector 305*s* with a serrated perimeter on the internal end 305. The inner connector 305 and the outer connector 325 can be connected by an arcuate bridging arm 310. The connector 305 may be directly or indirectly attached to the laterally extending member 117, typically to an upper or lower surface thereof.

Figure 2C:
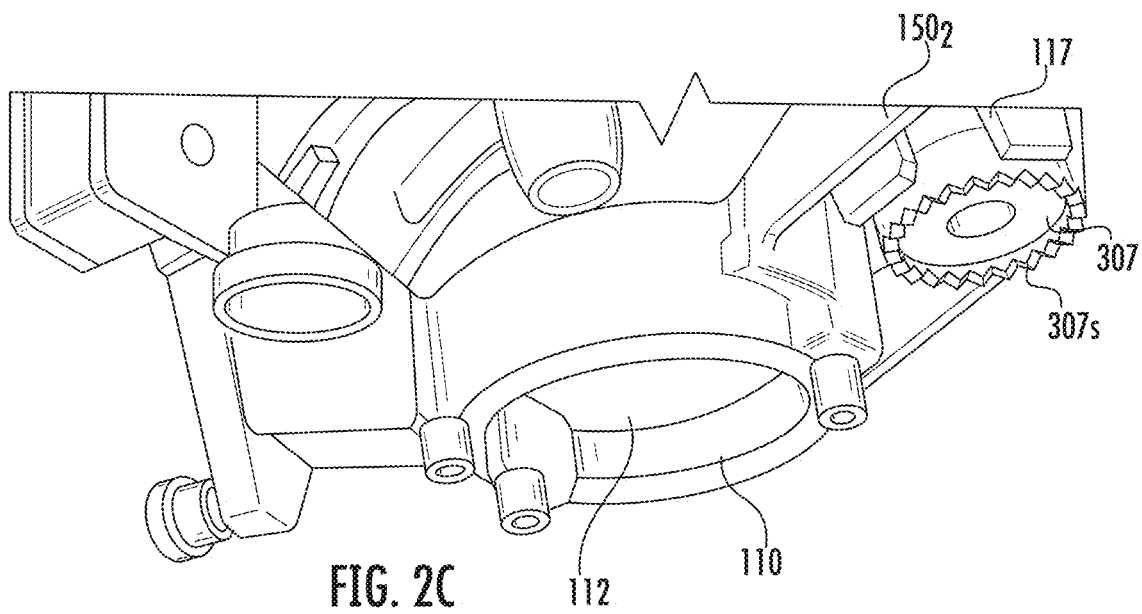
FIG. 2C is a side, bottom perspective view of an exemplary base of a trajectory frame assembly according to embodiments of the present invention.

As shown in FIG. 2C, for example, in some embodiments, a coupling starburst connector 307 with a perimeter with serrated edges 307*s* can be used to attach the connector 305 of the bracket 300. The coupling starburst connector 307 can be adhesively attached to or moldably formed onto or into the laterally extending member 117 and used to matably attach to the connector 305. The coupling connector 307 may have a height dimension that is less than that of the end connector 305.

The bracket 300 can be made in different lengths with the same or a different radius of curvature and each can be interchangeably held by the trajectory frame assembly 100. FIGS. 8A-8D illustrate an example of a "short" version and FIGS. 9A and 9B illustrate a "longer" version, for example. As shown, each can have the same connectors 305, 325 but a different length bridging arm 310.

The laterally extending members 117 can optionally hold toroidal or other two or three dimensionally shaped fiducials on an upper surface thereof, in some embodiments (not shown).

In some embodiments, the reference bracket 1200 can be mounted directly to the top and/or bottom of the laterally extending member(s) 117 held by the base and these embodiments do not require a separate bridging arm, for example.

Figure 3:
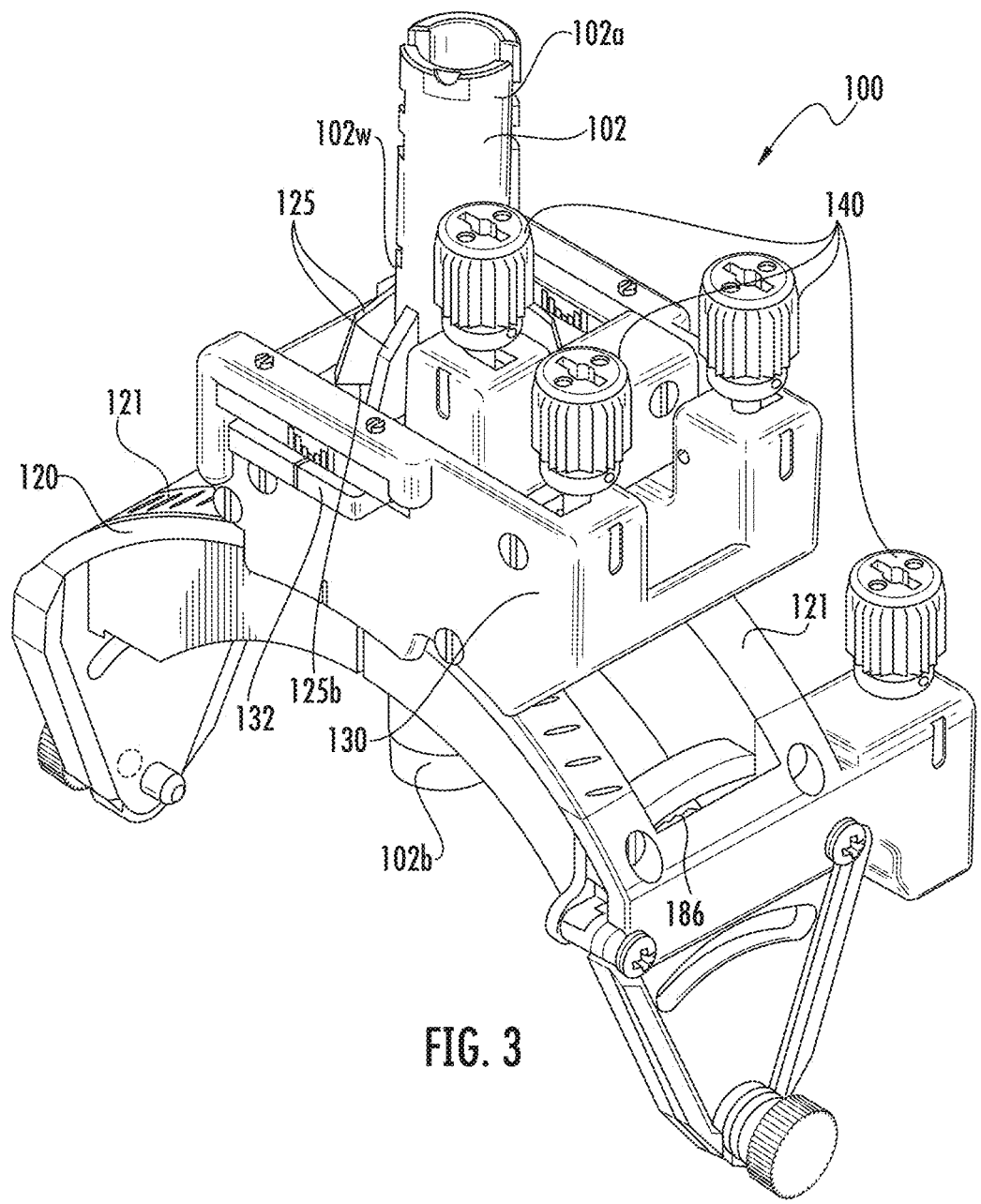
FIG. 3 is a top perspective view of a platform with an X-Y table and yoke of a trajectory frame assembly according to embodiments of the present invention.

Referring to FIGS. 1 and 3, the trajectory frame assembly 100 can include circumferentially spaced apart fins 125 attached to an outer wall 102w of the support column 102. The fins 125 can extend radially outward from the wall 102w of the support column 102, typically so that a bottom surface 125b (FIGS. 3, 11A, for example) resides against an upper surface 132u of the X-Y table 132. Exemplary features of the fins 125 will be discussed further below.

Figure 4A:
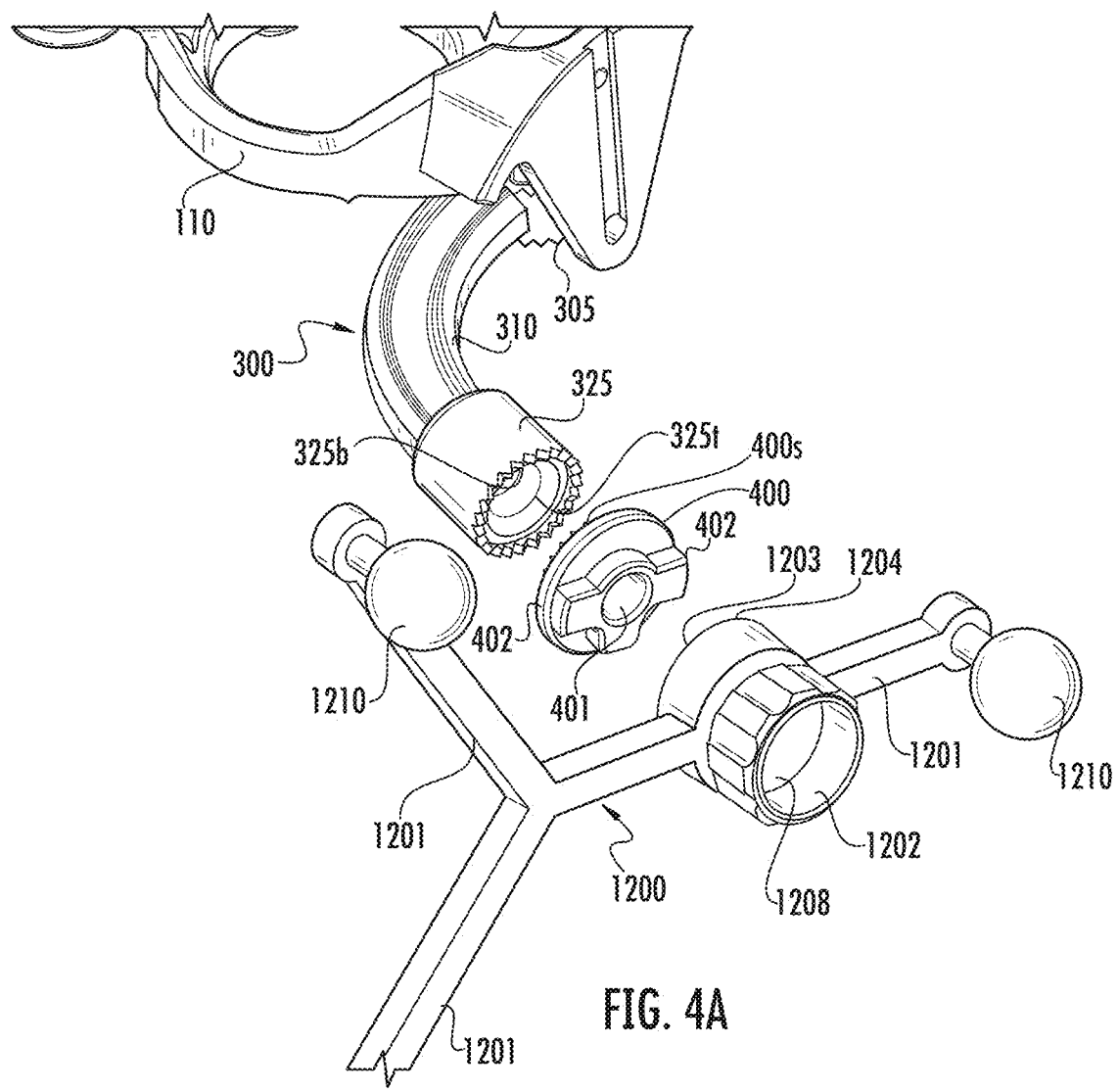
FIG. 4A is a partial, front perspective exploded view of a reference bracket and reference frame for a trajectory frame assembly according to embodiments of the present invention.
Figure 5:
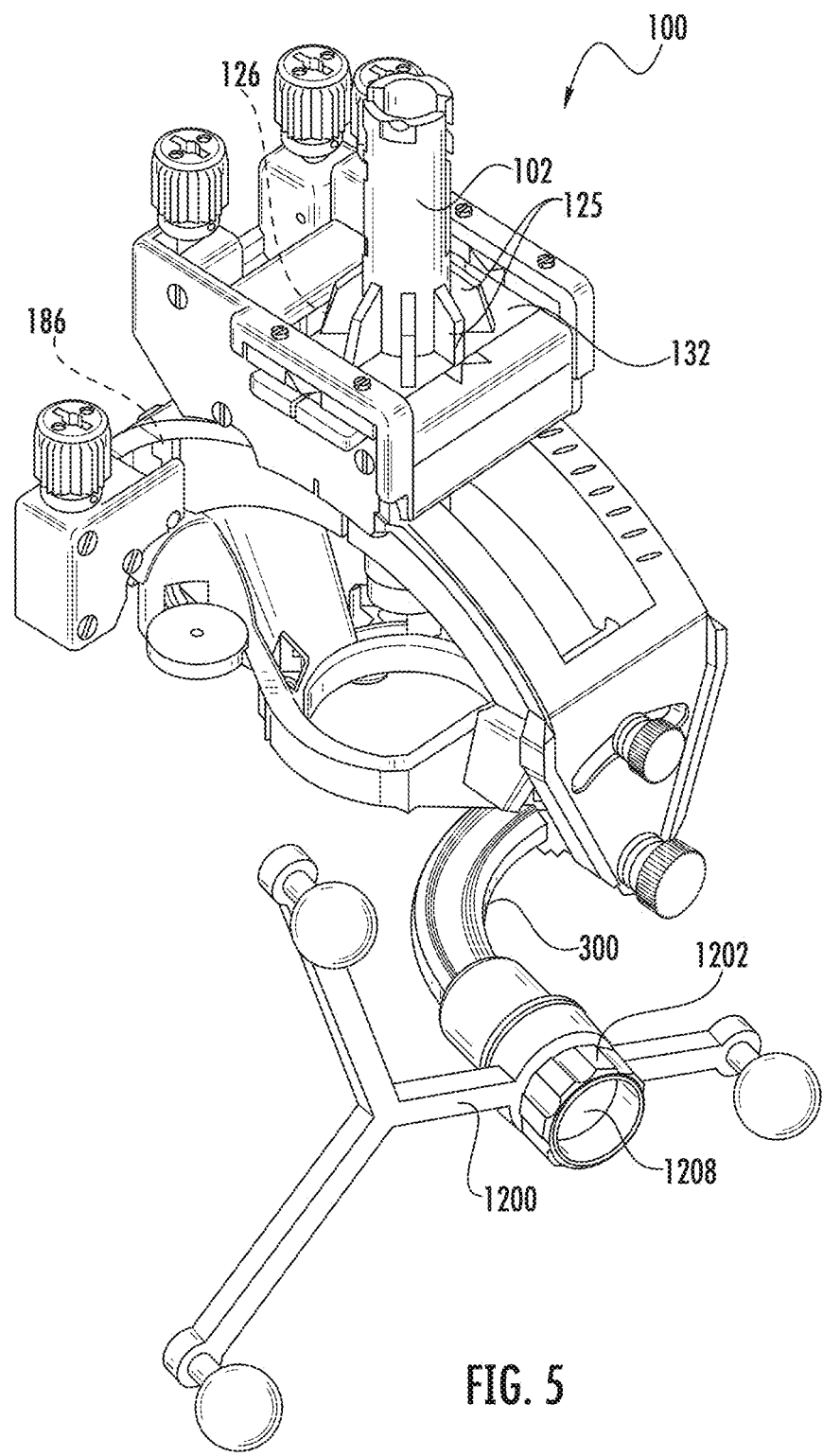
FIG. 5 is a front, side perspective view of a trajectory frame assembly with a reference bracket and a reference frame according to embodiments of the present invention.

FIGS. 4A and 5 illustrate an exemplary reference frame 1200 attached to the trajectory frame assembly bracket 300. The reference frame 1200 can hold optical and/or EM tracking members/fiducials 1210 that allow a navigation to provide reference data for a medical procedure so as to register and/or track a position of the patient.

As shown in FIG. 4A, the reference frame 1200 can include a plurality of linearly extending arms 1201 and an attachment member 1202 with a cylindrical short cavity 1208 and a fixation member 1203 extending under the cavity 1208, typically a threaded shaft, pin or screw, facing the connector 325.

Figure 4B:
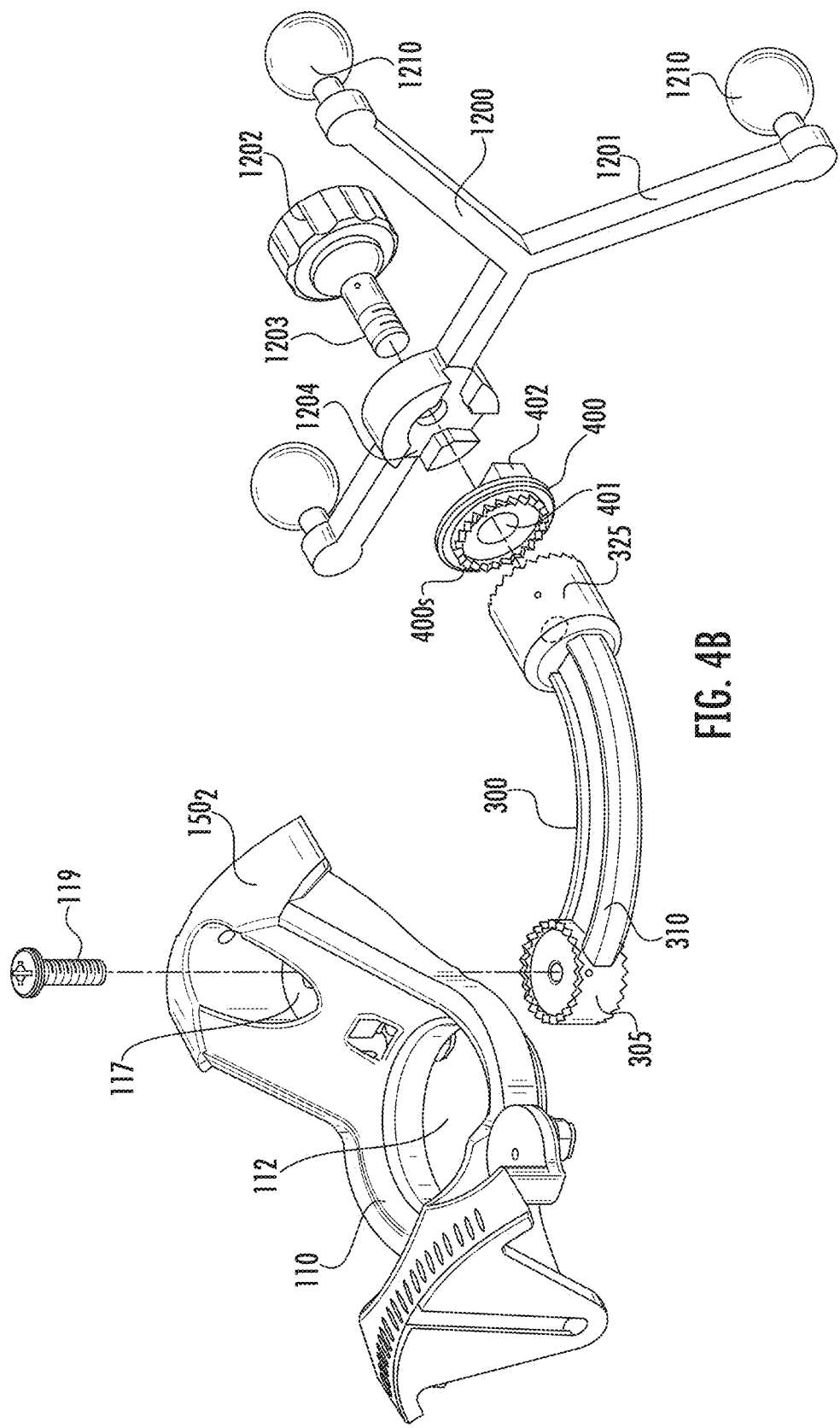
FIG. 4B is a side perspective partial exploded view of the reference bracket and reference frame shown in FIG. 4A according to embodiments of the present invention.

As shown in FIGS. 4A and 4B, a coupler 400 can be used to attach the connector 325 to the attachment member 1202. The coupler 400 can have an open through channel 401 and a primary surface with a serrated shape 400s that can face and engage the serrated shape 325s of the connector 325. The serrated shape 400s can reside inside an outer perimeter of the coupler 400p and encircle the through channel 401. An opposing primary surface of the coupler 400 can have alignment members or features 402 that mate with corresponding recessed features/members 1204 (FIG. 10C) in the fixation member 1202 to lock the coupler in a desired orientation relative to the attachment member 1202. The fixation member 1203 extends through the coupler 400 and engages female threads in the connector 325.

As shown in FIG. 4A, the alignment members 402 are three raised radially extending ribs or surfaces but other configurations may be used including lesser numbers of raised surfaces. Also, the reverse alignment feature configuration can be used so that the coupler alignment features 402 are recessed and engage projecting mating ribs or surfaces 1204 in the attachment member 1202.

Figure 8A:
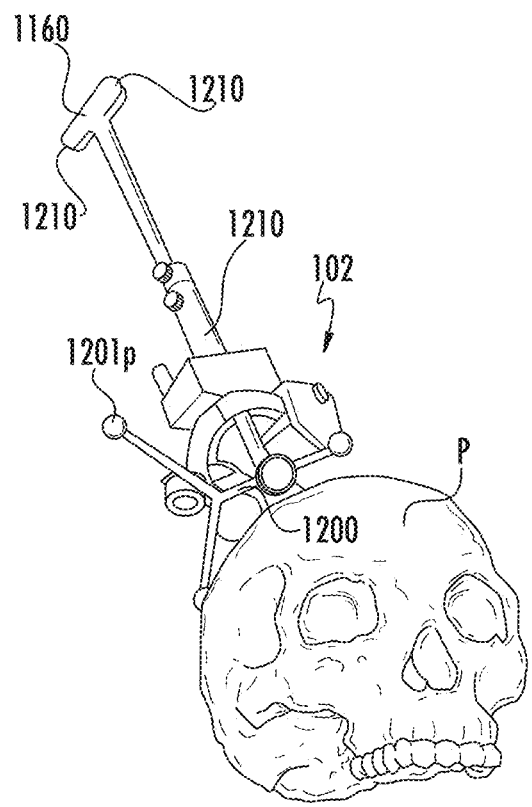
FIGS. 8A-8D illustrate the trajectory frame assembly attached to a "short" reference bracket and reference frame with a tracking probe in an exemplary location on a skull of a prophetic patient.
Figure 8B:
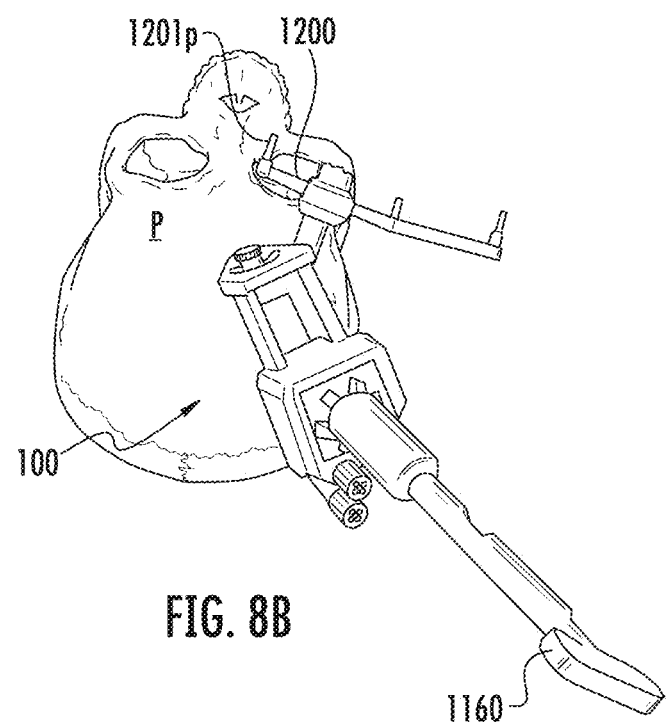
Figure 8C:
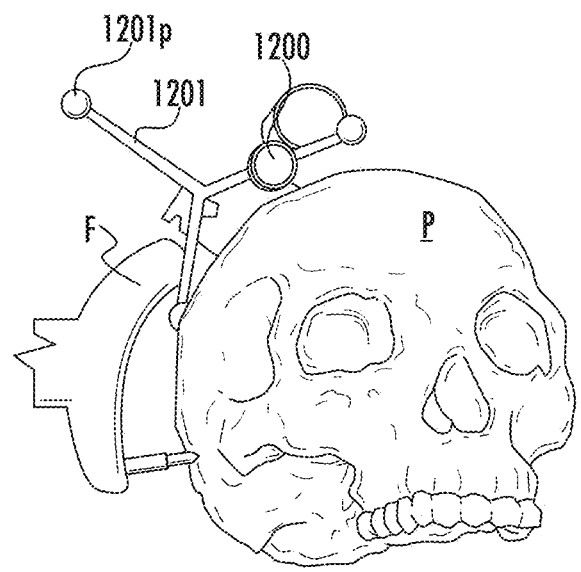
Figure 8D:
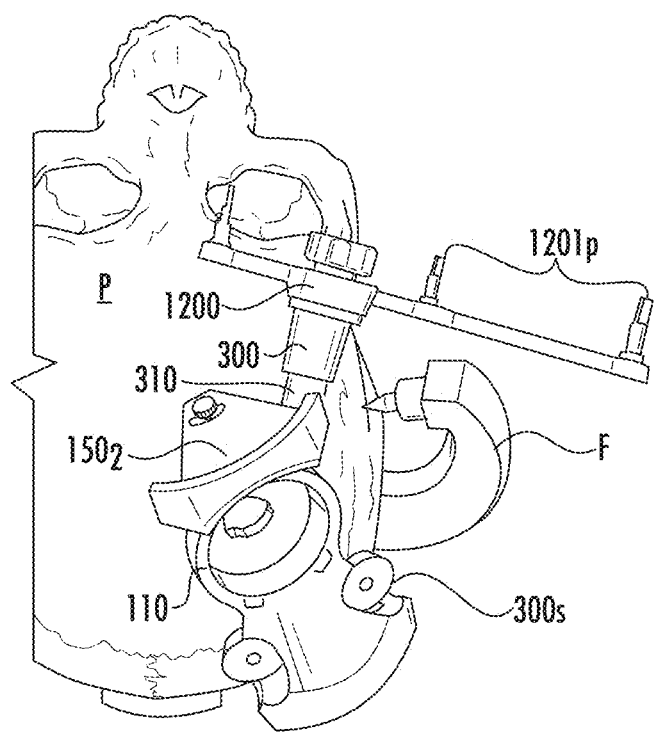
Figure 9A:
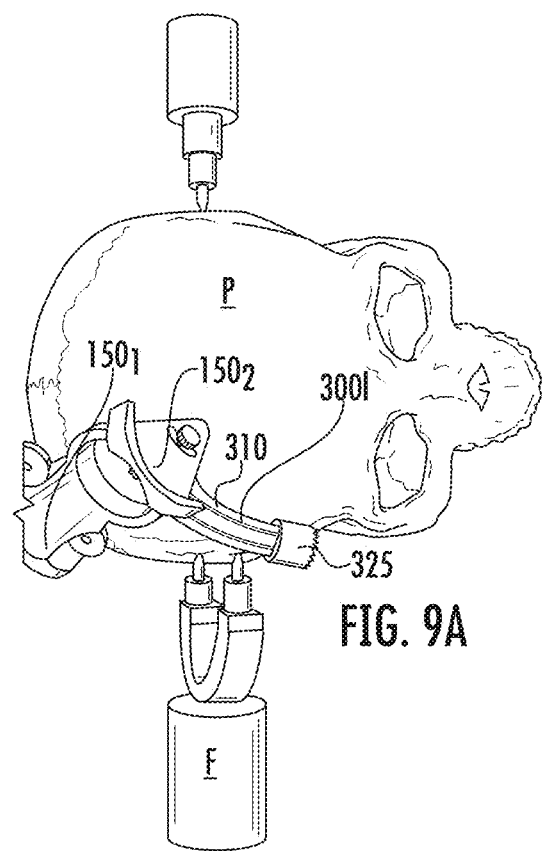
FIGS. 9A and 9B illustrate the trajectory frame assembly attached to a "longer" reference bracket and reference frame with a tracking probe in an exemplary location on a skull of a prophetic patient.
Figure 9B:
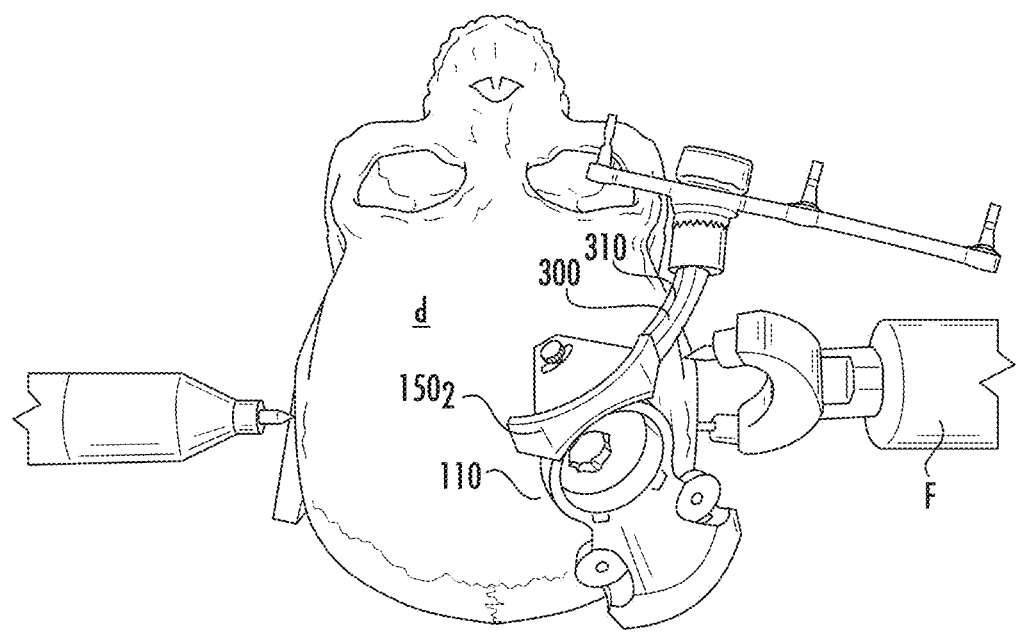

In some embodiments, the CT or MRI imaging modality tracking members and/or fiducials 1210 are held by the reference frame 1200 via prongs 1201p on the arms 1201 (FIGS. 8A, 8B, 9A, for example). The arms 1201 and/or members 1210 can comprise CT visible materials or hybrid materials that are visible in both MRI and CT images, for example. The fiducials and/or tracking members 1210 can be flat or spherical or have other shapes and may have a reflective coating. In some particular embodiments, the fiducials 1210 may comprise passive spheres such as those available from Northern Digital Inc. (ndigital.com) as NDI passive spheres that attach via snap-on attachment to posts on the arms 1201.

In some embodiments, the tracking members and/or fiducials 1210 can include or be doped with a substance having a high atomic number (Z), such as barium, titanium, iodine, silver, gold, platinum, iodine, stainless steel, titanium dioxide, etc. that provide good contrast on a CT or other radiographic imaging system. The tracking members and/or fiducials 1210 can include gadopentatate dimeglumine, gadoteridol, ferric chloride, copper sulfate, or any other suitable MRI contrast agent, such as described in chapter 14 of Magnetic Resonance Imaging, $2^{nd}$ ed., edited by Stark and Bradley, 1992, which is incorporated herein by reference.

In some embodiments, the tracking members and/or fiducials 1210 can be a solid material doped with a substance that provides good contrast using a first imaging modality (e.g., CT). A hygroscopic outer coating can be formed thereupon. The coating permits soaking up a fluid that provides a good contrast using a second imaging modality (e.g., MRI). In some embodiments, the tracking and/or fiducials 1210 comprise reflective members such as, for example, spherical locators and may have a body, coating, tape and/or outer surface that is reflective of light or other electromagnetic energy. Consequently, it is also locatable by the operating room camera 10c (FIG. 24) in an optical positioning system that is coupled to the image-guided workstation 30 (e.g., during patient registration). In one such example, the outer surface of the tracking members 1210 includes light-reflective micro-spheres (e.g., embedded in an adhesive covering). In another such example, the outer surface can include or be covered with a reflective coating or material, such as, for example, an adhesive-backed light-reflective tape, such as SCOTCHLITE® 9810 Reflective Material Multipurpose Tape sold by Minnesota Mining and Manufacturing Co. ("3M®"), of Saint Paul, Minn.

Figure 6:
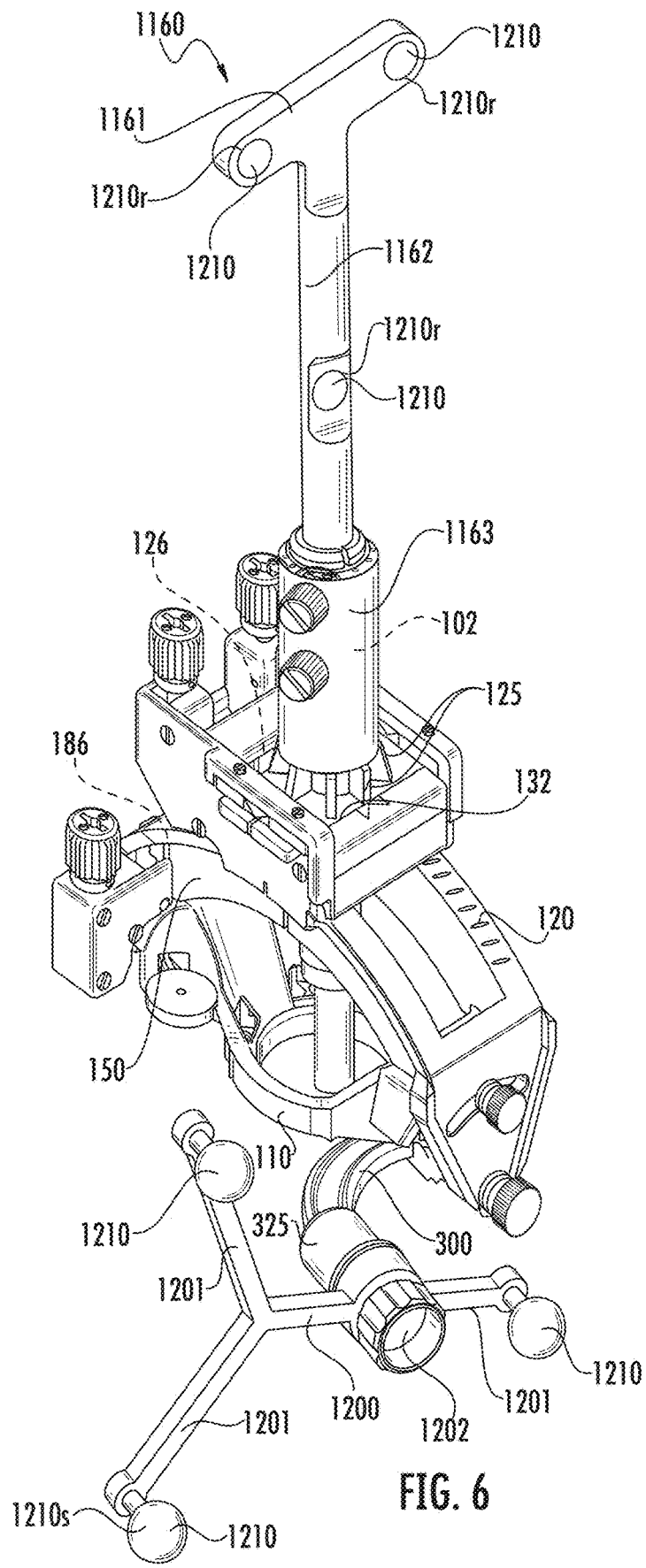
FIG. 6 is a front, side perspective view that illustrates the trajectory frame assembly shown in FIG. 5 holding an exemplary tracking probe according to embodiments of the present invention.

In some embodiments, the trajectory frame assembly 100 and/or other cooperating tools such as, for example, a tracking probe 1160 can include tracking members and/or fiducials 1210 as shown in FIG. 6. These tracking or fiducial markers or members 1210 can be tracking (e.g., reflective) optical or EM markers and/or fiducials, shown as three reflective flat circular shapes in FIGS. 6 and 8A, for example, held above the platform 132 by the support column 102. The tracking probe 1160 can have an elongate body 1162 under a laterally extending segment 1161. The reference bracket 1200 can reside below and laterally spaced apart from the reflective markers 1210r of the tracking probe 1160. The reference bracket 1200 can also or alternatively hold spherical reflective or optically detectable members 1210s.

The tracking probe 1160 can be releasably secured to the support column 102. As shown, an external collar 1163 which is open to environmental conditions and visually accessible during use (in position in the support column 102) can reside over the upper end of the support column, typically over an upper portion of one or more of the fins 125 but above lower ends of the fins 125.

Figure 7A:
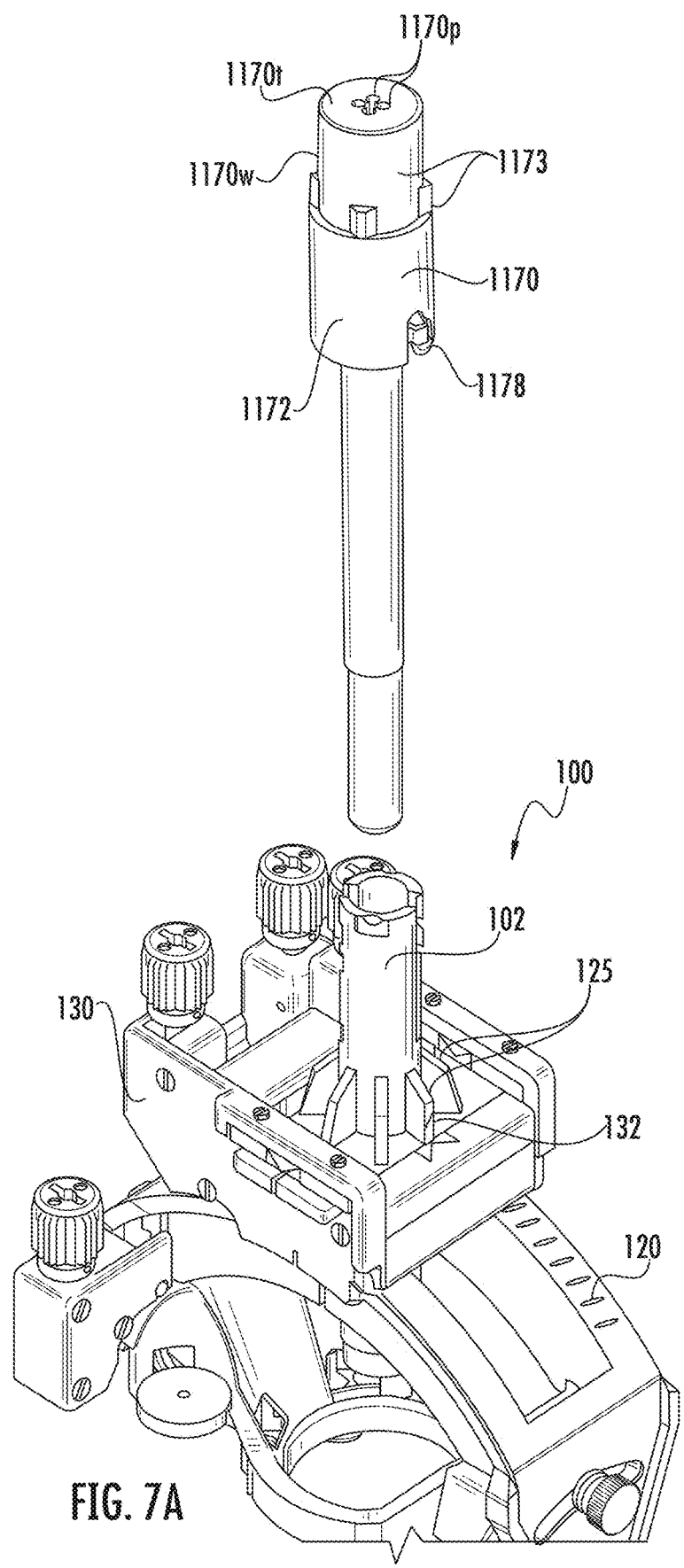
FIG. 7A is a front, side perspective view that illustrates the trajectory frame assembly shown in FIG. 5 (serially, interchangeably) receiving an exemplary microelectrode driver adapter according to embodiments of the present invention.
Figure 7B:
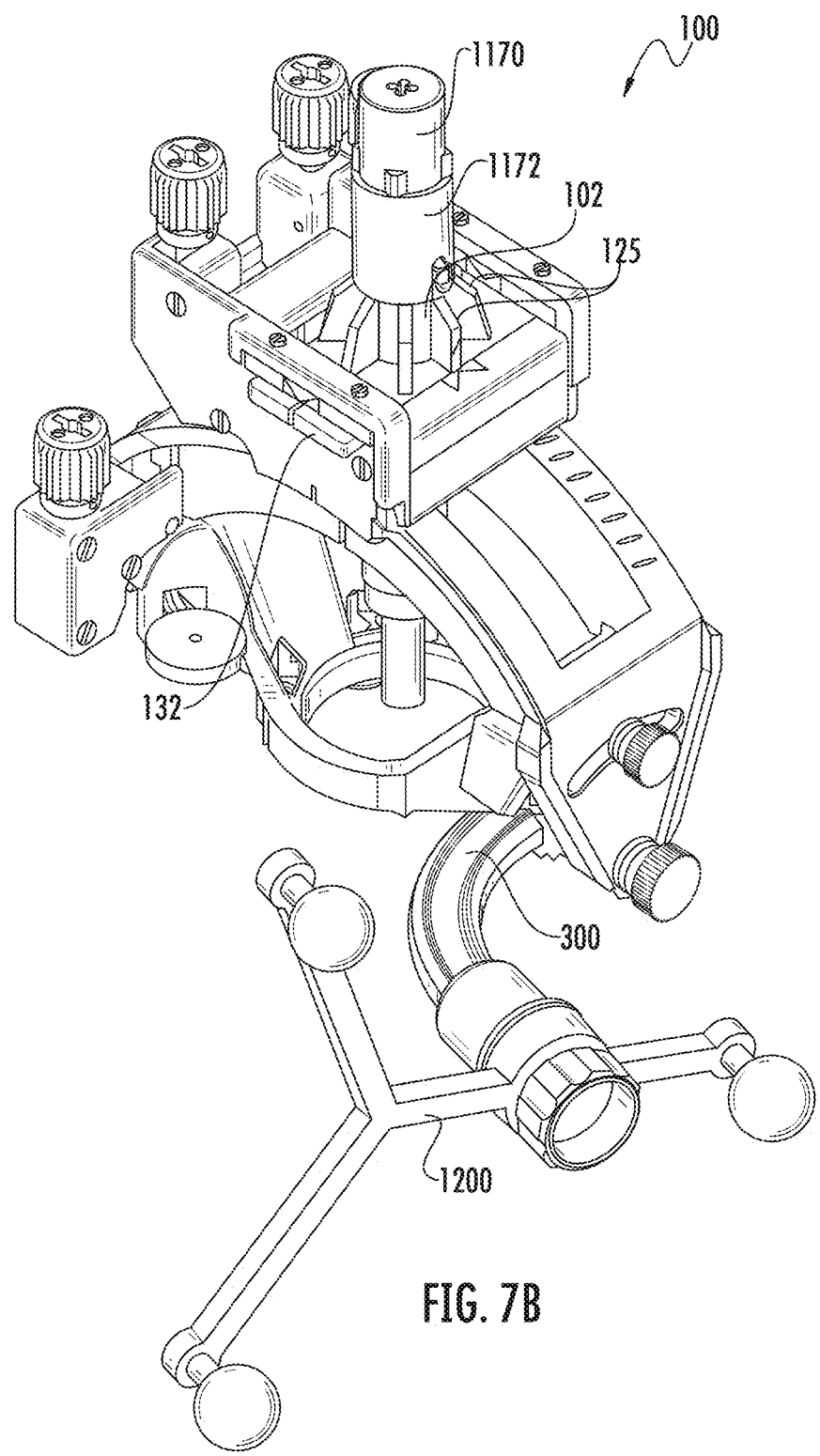
FIG. 7B shows the trajectory frame assembly in FIG. 7A secured to the driver adapter according to embodiments of the present invention.
Figure 7C:
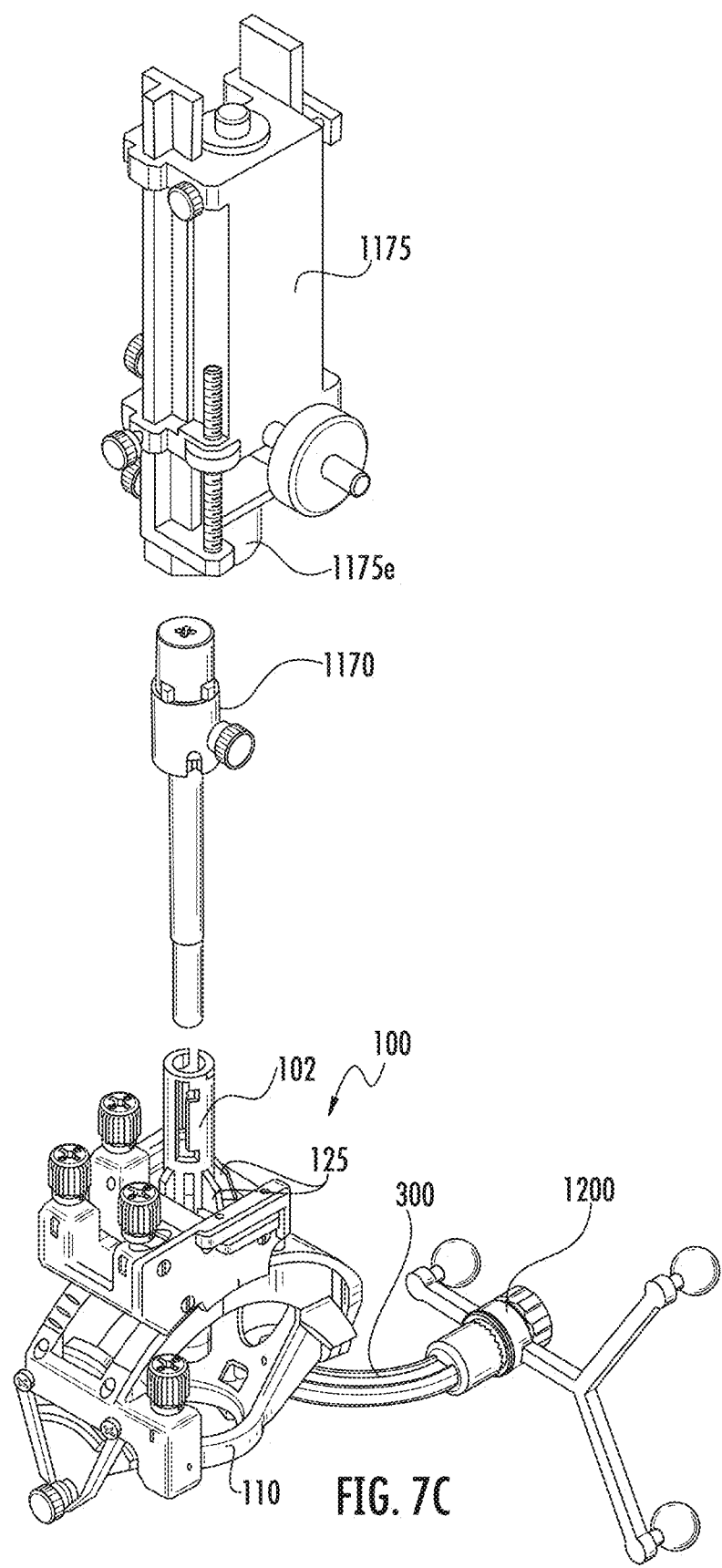
FIG. 7C is a back, side perspective view of the trajectory assembly with the driver adapter shown in FIGS. 7A and 7B and aligned with a driver according to embodiments of the present invention.

FIGS. 7A and 7B illustrate that the support column 102 can releasably secure a microelectrode driver adapter 1170 that can hold a manual or electromechanical driver to drive microelectrodes through ports 1170p in the adapter and into position in the brain, for example. The ports 1170p may be provided in a flat top surface 1170t of the adapter 1170. The ports 1170p merge into elongate open and parallel channels extending through the adapter 1170. The adapter 1170 can have an external collar 1172 that can slidably engage the support column 102. The adapter 1170 can have radially extending tabs 1173 that extend outward a distance from the outer wall of the adapter 1170w, above the collar 1172.

Figure 7D:
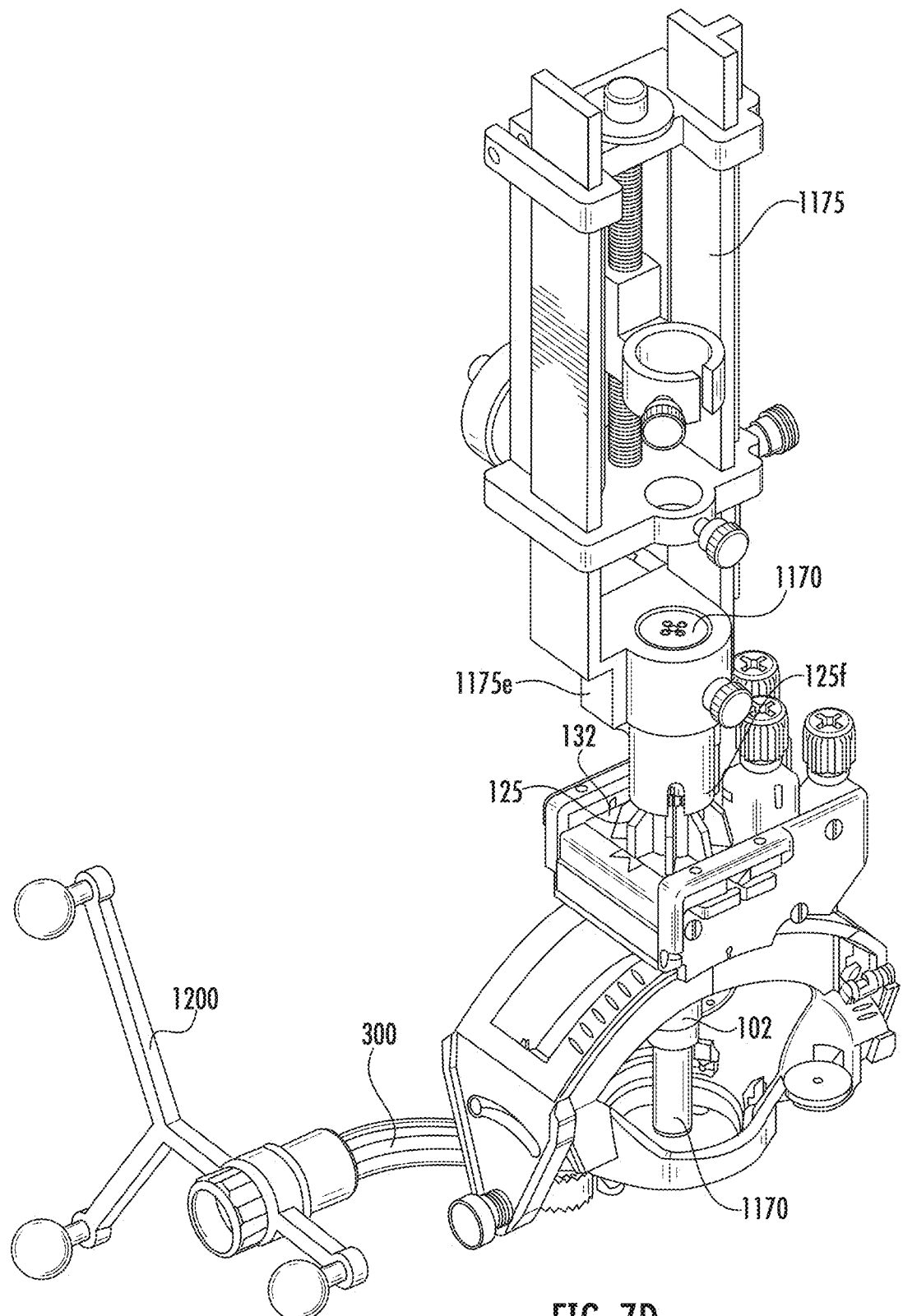
FIG. 7D is a front, side perspective view that illustrates the driver in FIG. 7C attached to the adapter in the trajectory assembly according to embodiments of the present invention.

The lower end of the driver 1175e can reside over the top end of the adapter 1170 with the ports flush at the upper surface thereof (FIG. 7D).

FIGS. 7A-7D show the trajectory frame assembly 100 with the guide/support column 102 releasably holding a microelectric (MER) probe driver adapter 1170, typically used for "awake" brain surgeries, according to embodiments of the present invention. The adapter 1170 can have outwardly extending lugs 1178 that engage slots in the guide 102. The radially extending tabs 1173 may define a stop so that the driver 1175 engages the probe drive adapter at a desired position. The MER probe drive adapter 1170 can matably engage a drive system 1175 (FIG. 7C) such as the NEXDRIVE® drive system. Other electronic and/or manual drivers may be used.

To be clear, it is also contemplated that other attachment configurations may be used to releasably secure the tracking probe and the MER drive adapter 1170 to the support column 102.

FIGS. 8A-8D illustrate a reference frame 300 which is a shorter version 300s of the reference bracket 300 shown in FIGS. 9A and 9B (the latter of which can be referred to as a "long" reference bracket 300l), for example. Each reference bracket 300s, 300l can be attached to the base of the trajectory frame 110, typically to a laterally extending member 117 to extend forward, and radially inward, toward the nose of a patient P. In the position shown on the patient (which can vary based on target anatomical treatment sites), the longer version (FIG. 9A) positions the reference frame 1200 in a plane that is a distance in front of the orbital sockets of the skull of a patient P while the shorter version 300s positions the reference frame 1200 in a plane behind the orbital sockets of the patient P.

Figure 26:
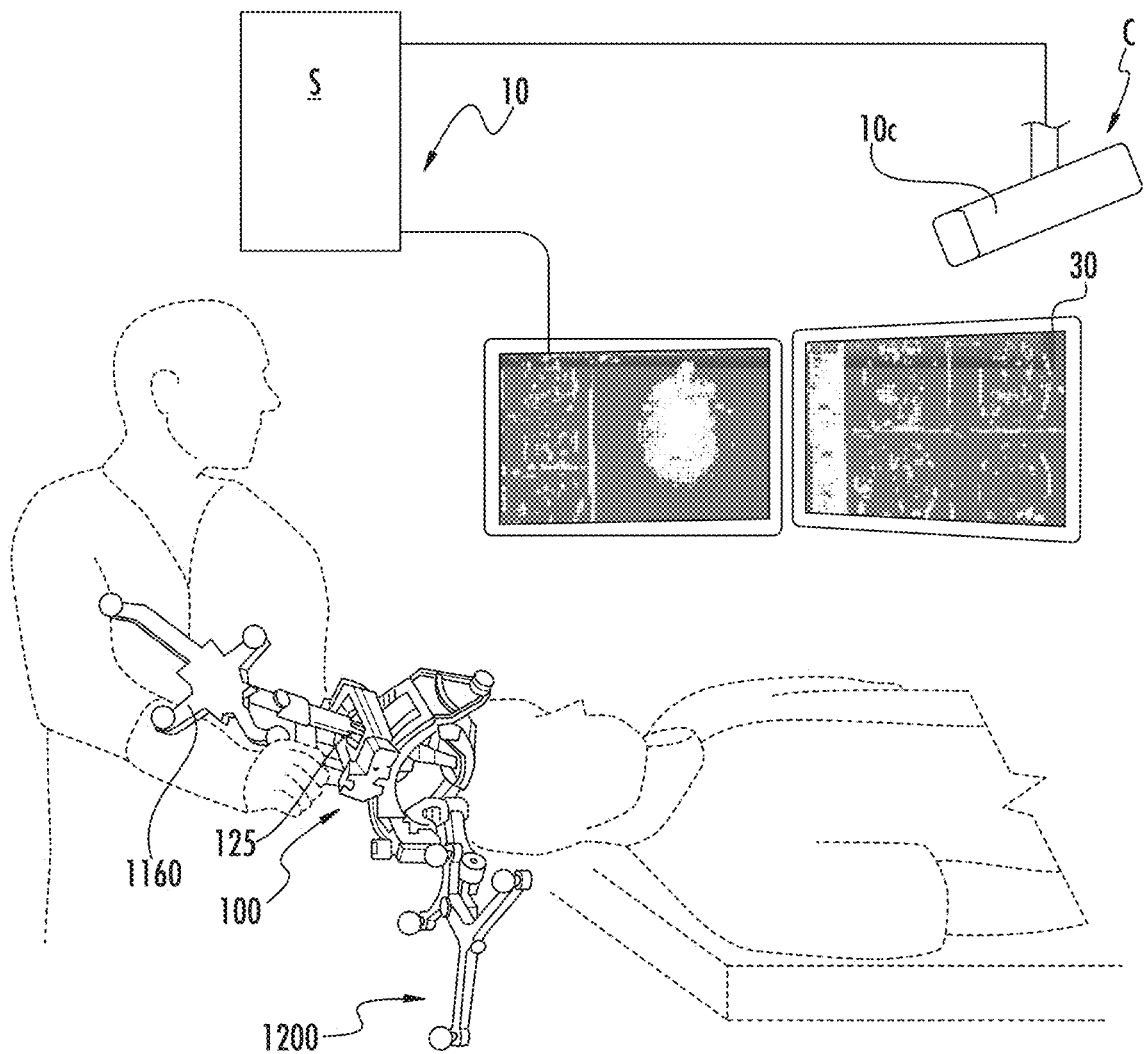
FIG. 26 is a schematic illustration of a camera-based navigation system according to embodiments of the present invention.

FIG. 26 also illustrates that the outer end of the bridging arm 310 can provide two adjacent outer connectors $325_1$, $325_2$, with serrated surfaces 325s, each with bores 325b, one with an axis A-A that is angularly offset, typically orthogonal, to the other A-A. The axis A-A of connector $325_1$ can be parallel to that of the inner connector 305.

Figure 10A:
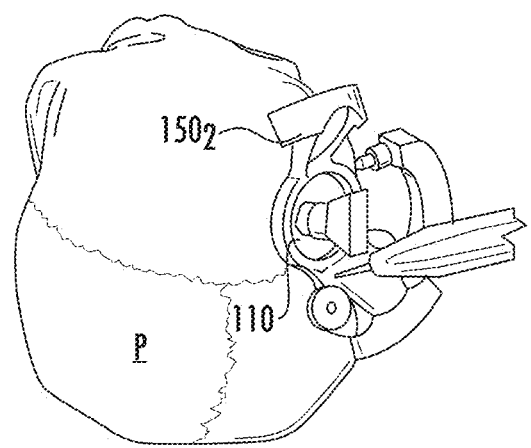
FIGS. 10A-10C show an exemplary assembly sequence for attaching a base to a reference bracket and reference frame according to some embodiments of the present invention.
Figure 10B:
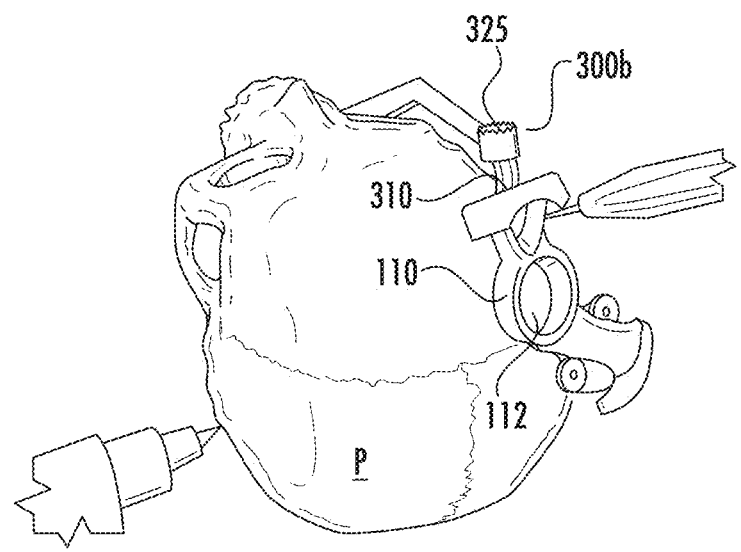
Figure 10C:
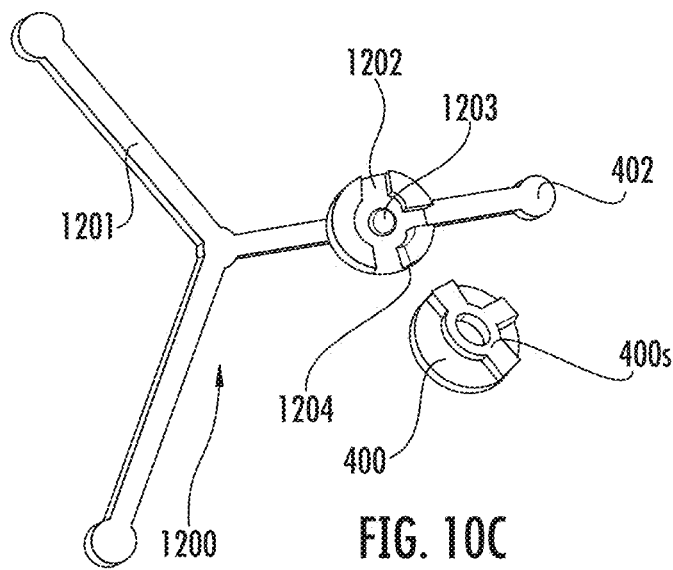

FIGS. 10A-10C illustrate an exemplary sequence of operations that can be used to assemble the trajectory assembly 100 and attach the assembly 100 to the patient P. The base 110 with the arcuate arms 150 can be positioned (e.g., centered if using a centering tool over an entry into the skull) and attached to a patient (FIG. 10A). The reference bracket 300 can be attached to the base 110 (FIG. 10B). The coupler disk 400 can be placed on the reference frame 1200 with the key features 1204, 402 aligned. The reference frame 1200 can be attached to the connector 325 of the bracket 300, typically by threading fixation member 1203 though the coupler 400 and into the connector 325 with the serrated segments 325s, 400s, engaged. The remainder of the trajectory frame assembly 100 (i.e., the yoke with the support column 102) can be attached to the base 110.

FIGS. 11A-11C, 12, 13A and 13B illustrate a support column 102 with a fin arrangement or array 125a. As shown, in FIG. 13A, for example, the fins 125 facing the gear teeth 126 (that engage a worm to move the table front to back) may have a shorter length from the outerwall 102w of the support column 102 to its outermost edge 125e, than some or all of the other fins 125, such as the ones on the opposing long side of the X-Y table 132. As shown, there are eight circumferentially spaced apart, radially extending fins 125.

Centerlines of some adjacent fins 125 can be positioned to be circumferentially spaced apart at an angle "a" that is between 15 degrees and 90 degrees, typically 45 degrees apart. Lesser or greater numbers of fins 125 may be used and can be regularly or irregularly spaced apart. One or more of the fins 125 can vary in shape from others and/or in length. The fins 125 can have a width or thickness that is between about 0.25 inches and 0.05 inches, more typically about 0.10 inches to about 0.06 inches, such as about 0.10 inches, about 0.095 inches, about 0.09 inches, about 0.085 inches, about 0.08 inches, about 0.075 inches, about 0.07 inches, about 0.065 inches.

The support column 102 may have a length between about 3-6 inches, such as about 3 inches, about 4 inches, about 5 inches and about 6 inches in some embodiments. The fins 125 can have an interior side that resides adjacent to, and may attach to, the outer wall of the support column 102w with a height "H" (FIG. 11C) that is between about 0.25 inches and 1 inch. Typically the horizontal length "L" (FIGS. 13A, 14C) is between about 0.15 inches and 1 inch, more typically between about 0.2 inches and 0.75 inches, such as about 0.4 inches about 0.45 inches, about 0.475 inches and about 0.5 inches. This length L can be particularly suitable for a column support 102 with a height "d" above the support table 132 that is between 1.5 and 3 inches, such as about 1.74 inches.

The fin 125f adjacent a side of the gear teeth 126 can have a shortest radially extending length, typically between 0.10 and 0.70 inches, such as about 0.077 inches, in some embodiments.

Figure 11A:
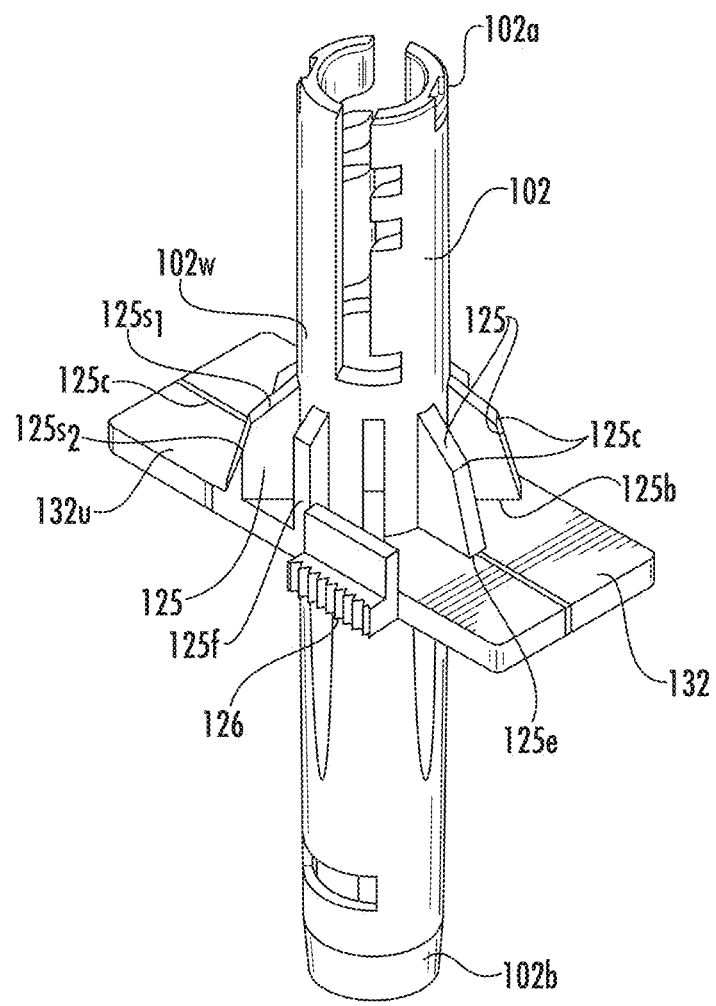
FIG. 11A is a side perspective view of a support column with fins according to embodiments of the present invention.
Figure 11B:
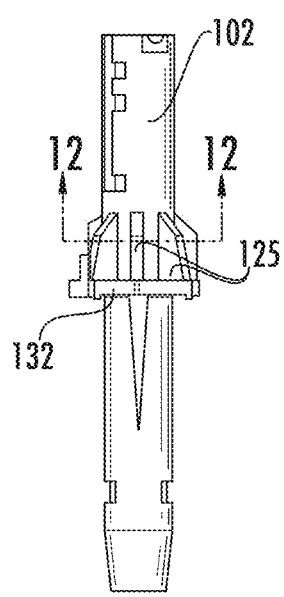
FIGS. 11B and 11D are short side views of the support column shown in FIG. 11A.
Figure 11C:
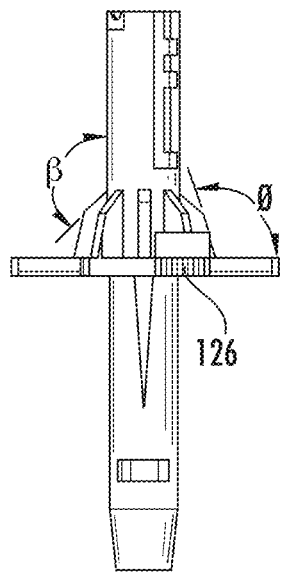
FIG. 11C is a long side view of the support column shown in FIG. 11A.
Figure 11D:
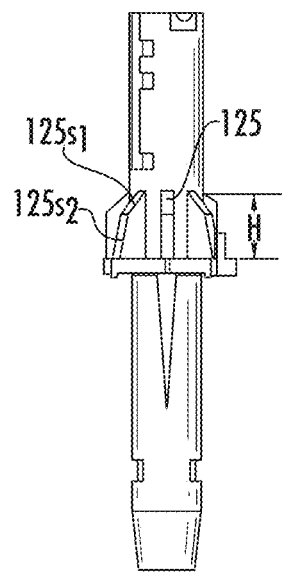
Figure 12:
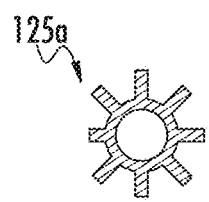
FIG. 12 is a section view taken along lines 12-12 in FIG. 11B.

All fins 125 may have a common maximal height H or some may have a greater or lesser height than others. As shown in FIGS. 11A and 11B, for example, at least some of the fins 125 have a first tapered down segment $125s_1$ that tapers down at a first angle β, to a second segment $125s_2$ that tapers down at a different angle "ø" relative to the first segment. The first angle β can be greater or less than the second angle "ø". The second segment $125s_2$ may have a greater length than the first segment $125s_1$. The first angle β can be about 135 degrees for a subset of the fins 125, typically 6 fins (where 8 fins are used). The second angle ø can be about 105 degrees for the same or a different subset of the fins 125, such as 4 fins (where 8 fins are used).

Figure 13A:
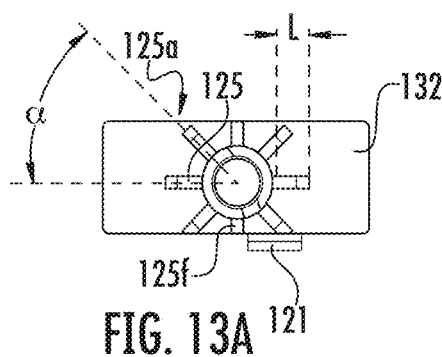
FIG. 13A is a top view of the support column shown in FIG. 11A.
Figure 13B:
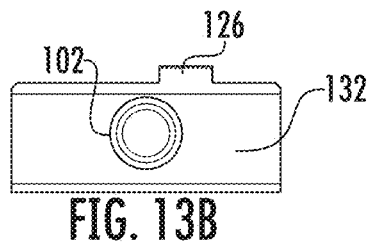
FIG. 13B is a bottom view of the support column shown in FIG. 11A.
Figure 14A:
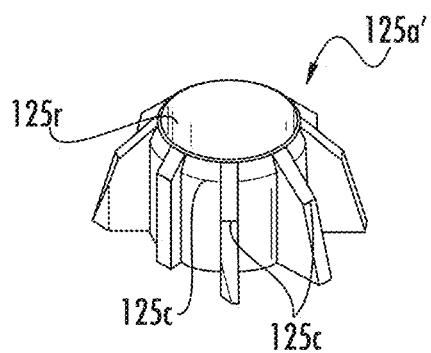
FIG. 14A is a side perspective view of a ring with fins that can be attached to a support column according to embodiments of the present invention.
Figure 14B:
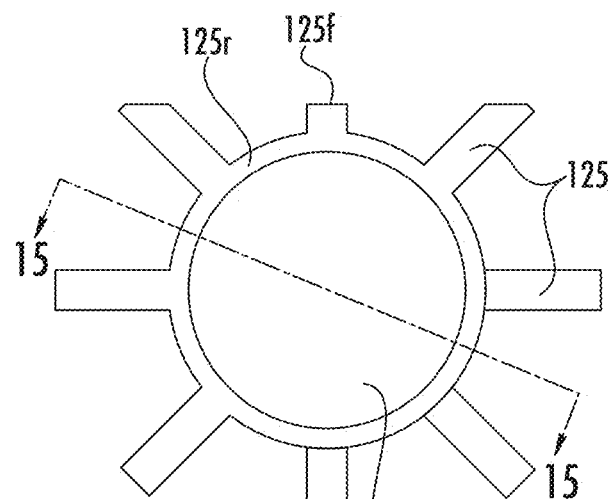
FIG. 14B is an enlarged bottom view of the ring shown in FIG. 14A.
Figure 14C:
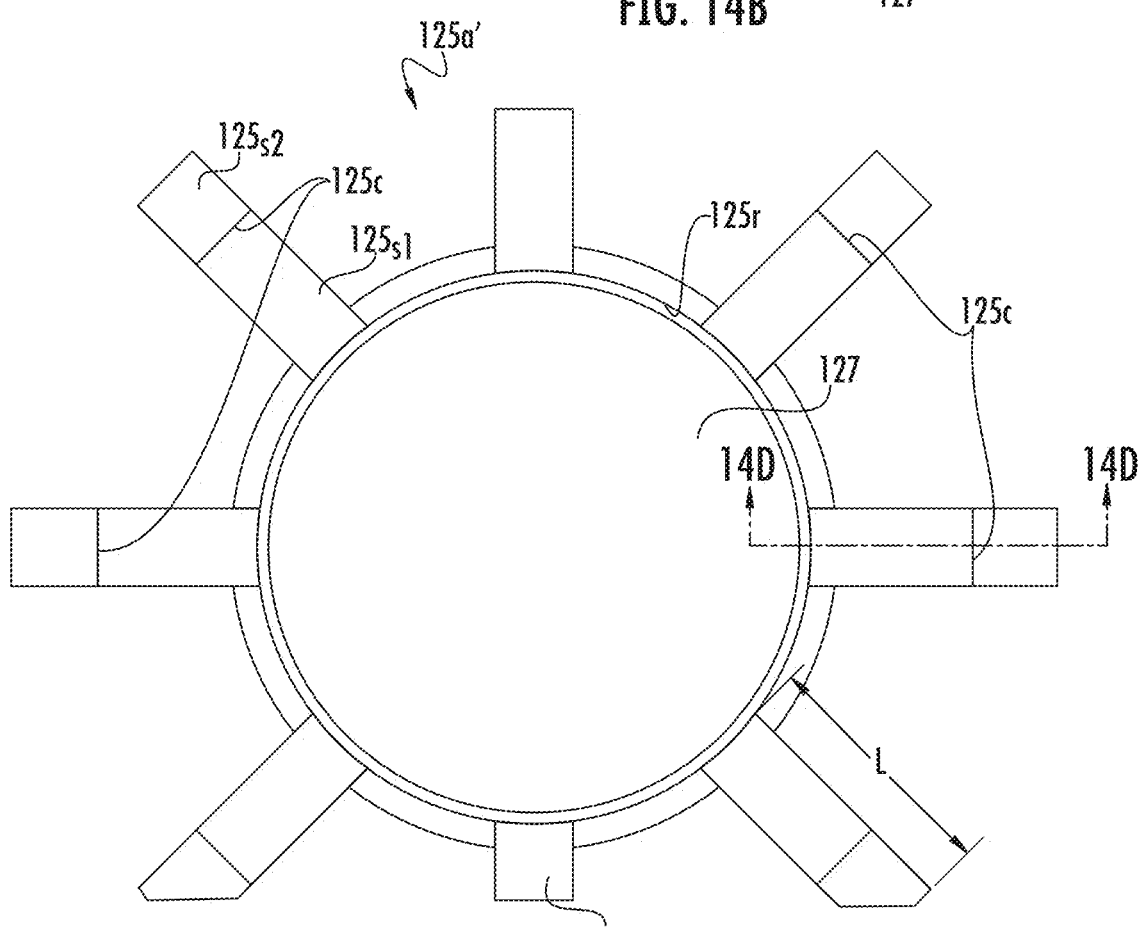
FIG. 14C is a greatly enlarged top view of the ring shown in FIG. 14A.
Figure 14D:
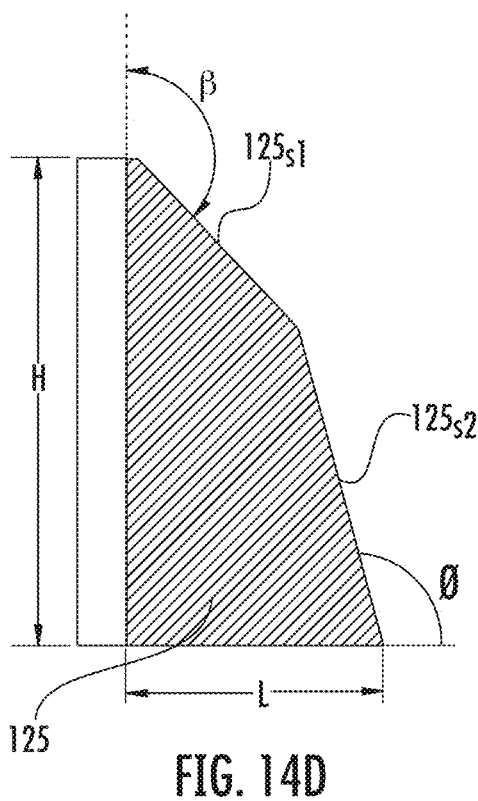
FIG. 14D is a section view taken along line 14D-14D in FIG. 14C.
Figure 15:
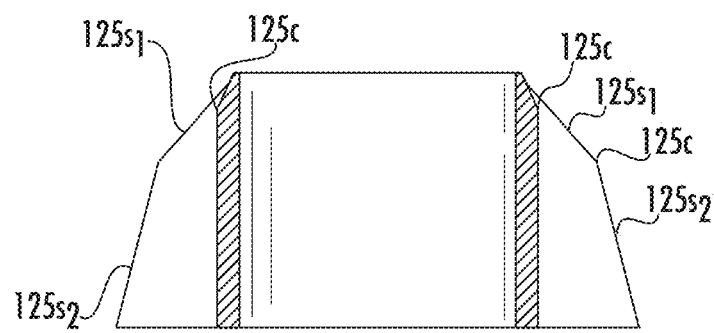
FIG. 15 is a section view taken along line 15-15 in FIG. 14B.

In some embodiments, as shown in FIGS. 13A and 13B, the column support 102 may not be centered with the laterally extending centerline with the laterally extending direction is the direction between the long sides of the support table 132 which in position is oriented to extend across the yoke arcs 121 (FIG. 1). As shown in FIG. 11A, for example, a plurality of the fins 125 can have a chamfered edge 125c between the first and second segments $125s_1$, $125s_2$. This chamfered edge 125c can reside at the same height and radial distance from the column 102 for some of the fins 125. This can provide a stop for the column 1163 of the adapter 1170 (FIG. 7B) and/or tracker probe 1160 (FIG. 6). In other embodiments, there can be a small gap between the fins 125 and the adapter 1170 (and also typically the driver held by the adapter 1170) so that there is no contact with the fins 125.

FIGS. 14A, 14B, 14C, 14D and 15 illustrate another embodiment of a fin array 125a'. In this embodiment, the fin array 125a' can be provided as a ring that can be attached to the support column 102 and/or X-Y table 132. The ring 125r can be provided as a single unitary (typically machined or molded) body or may be provided as two or more matable components to form the ring 125r (not shown). The fins 125f can have a similar configuration and dimensions described for the embodiments shown in FIG. 11A, for example. The ring 125r can have a through bore 127 sized and configured to extend about the outerwall of the support column 102w.

FIGS. 16A, 16B, 16C, 17, 18 and 19 illustrate a "longer" version 300l of a reference bracket 300. FIGS. 20A, 20B, 20C, 20D, 21, 22 and 23 illustrate a "shorter" version 300s of a reference bracket 300.

Figure 20A:
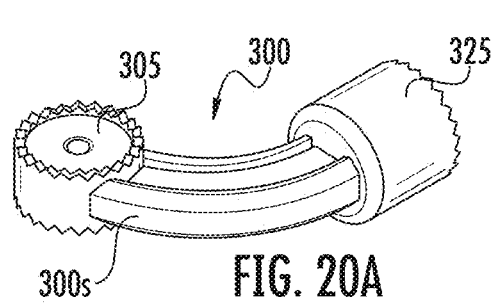
FIG. 20A is a side perspective view of a "long" reference bracket according to embodiments of the present invention.
Figure 20B:
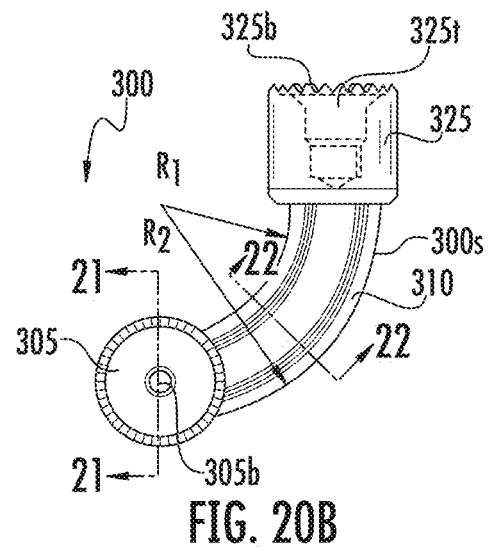
FIG. 20B is a top view of the bracket shown in FIG. 20A.
Figure 20C:
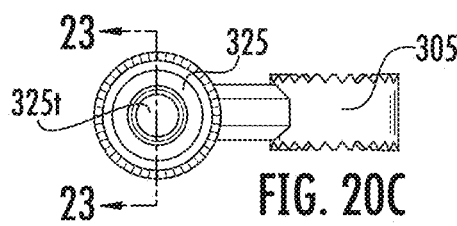
FIG. 20C is a side view of the bracket shown in FIG. 20A.
Figure 20D:
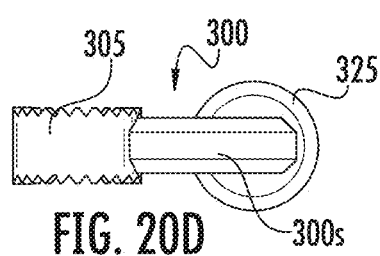
FIG. 20D is an opposing side view thereof.
Figure 21:
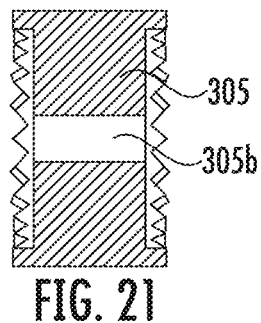
FIG. 21 is an enlarged section view taken along line 21-21 in FIG. 20B.
Figure 22:
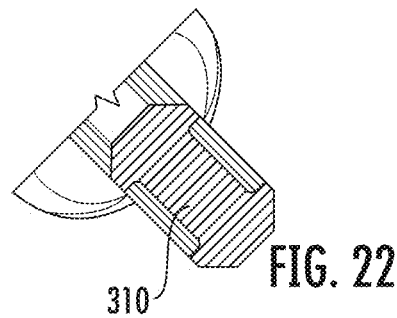
FIG. 22 is an enlarged section view taken along line 22-22 in FIG. 20B.
Figure 23:
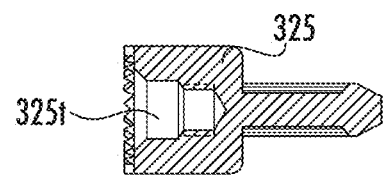
FIG. 23 is an enlarged section view taken along line 23-23 in FIG. 20C.

The bridging arm 310 can be arcuate as shown. The bridging arm 310 can have an inner perimeter with a first radius of curvature $R_1$ and an outer perimeter with a second radius of curvature $R_2$, measured from a line drawn from each of these arcs to a common point outside the bridging arm (FIGS. 16B, 20B). The differences between the first and second radii can be about 0.40 inches, in some embodiments. The long bracket 300*l* can position the centerlines of the connectors 305, 325 apart a distance of between about 2 inches and about 1.2 inches, typically about 1.302 inches. The short reference bracket 300*s* can position them apart a distance of between about 0.5 inches and about 1 inch, typically about 0.794 inches. The bridging arm 310 can have a width that is about 0.250 inches for each version of the bracket 300.

The bracket 300 can have a first radius of curvature R1 that is about 1.095 inches for the long version (FIG. 16B) and a first radius of curvature R1 that is about 0.595 inches for the shorter version (FIG. 20B).

The connector 305 can have a serrated portion 305*s* and a bore 305 which may be threaded. The connector 325 can have a serrated portion 325*s* and a bore that is typically threaded 325*t*. The connector 305 and the connector 325 may position the serrated segment so that an inner diameter is about 0.50 inches and an outer diameter is about 0.590 inches. The inner connector 305 may have a height that is less than that of the outer connector 325.

Figure 24:
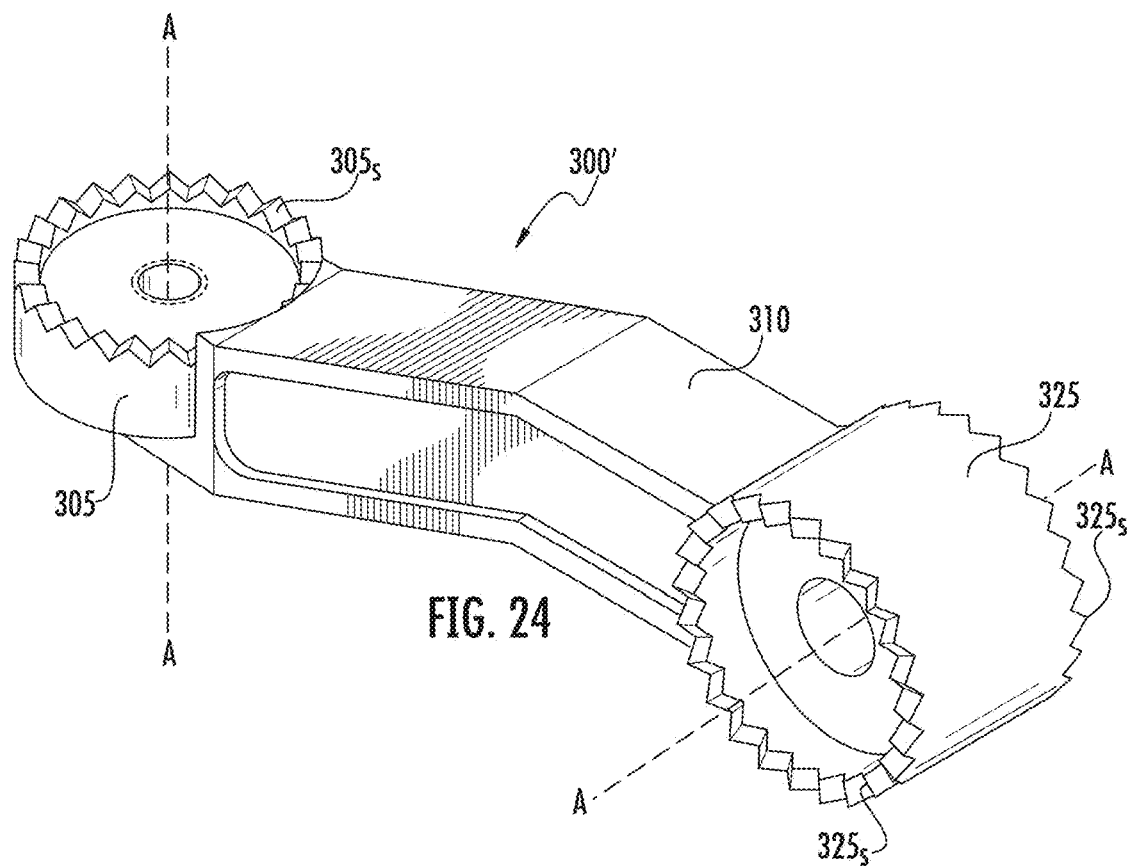
FIG. 24 is an enlarged side perspective view of an alternate embodiment of a reference bracket according to embodiments of the present invention.
Figure 25:
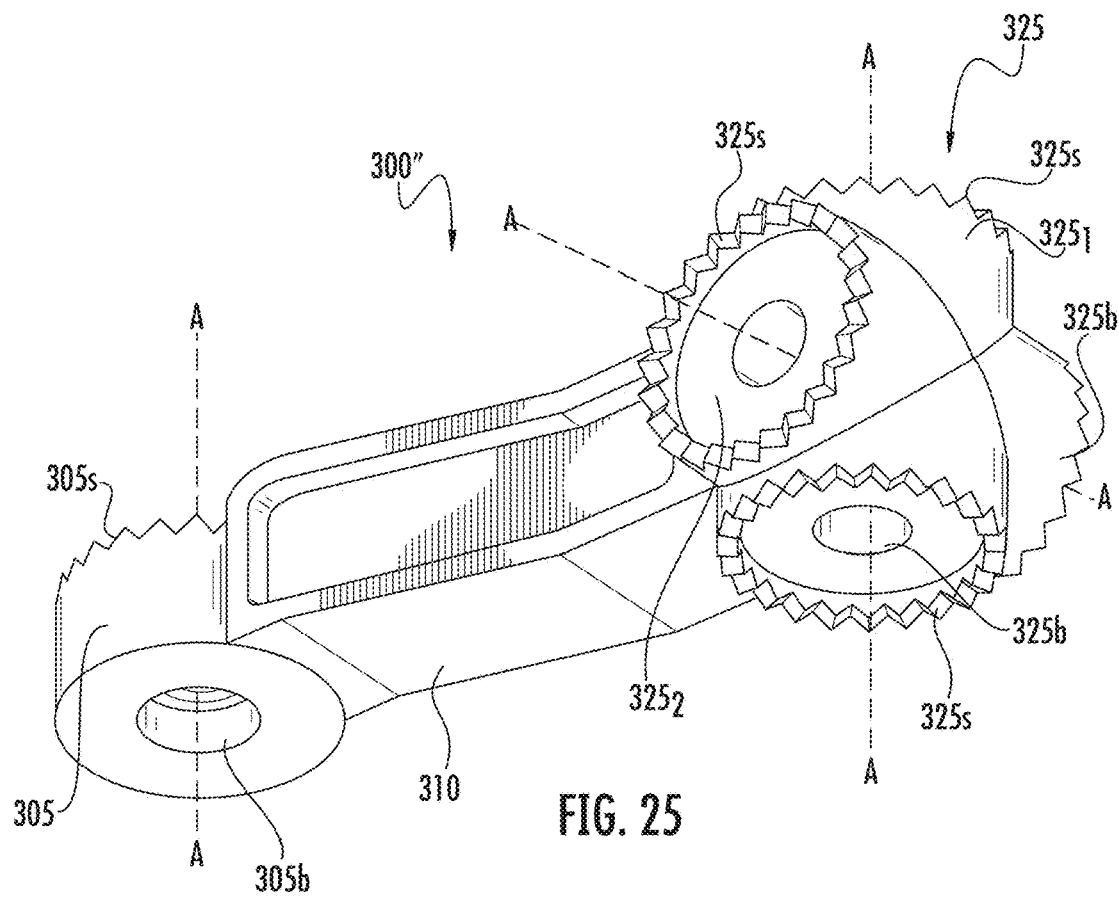
FIG. 25 is an enlarged side perspective view of yet another alternate embodiment of a reference bracket according to embodiment of the present invention.

FIGS. 24 and 25 illustrate alternate reference brackets 300', 300". The bridging arm 310 can have a length between 0.25 inches and 4 inches, typically between about 0.5 inches and 2 inches and/or can position centerlines of the connectors apart a distance of between 0.5 and 2 inches. FIGS. 24 and 25 illustrate that the connectors 305, 325 can have at least one serrated surface 305*s*, 325*s* and bores 305*b*, 325*b* one or both of which may optionally be threaded. FIGS. 24 and 25 illustrate that the bores can have an axially extending axis A-A that are at different angles, the axis A-A of the inner connector 305 can be upright while that of the outer connector may be 90-270 degrees offset therefrom.

Referring to FIG. 26, the navigation system 10 can include an imaging device or scanner S that can be used to acquire pre-, intra-, or post-operative or (near) real-time image data of a subject, such as a patient. It will be understood, however, that any appropriate subject can be imaged and any appropriate procedure may be performed relative to the subject and camera IGS systems can be used. The scanner may be a closed bore CT scanner or an O-Arm® imaging device sold by Medtronic Navigation, Inc. having a place of business in Louisville, Colo., USA. The scanner S may have a generally annular gantry housing and an image capturing portion. The image capturing portion may include an x-ray source or emission portion and an x-ray receiving or image receiving portion located generally or as practically possible 180 degrees from each other and mounted on a rotor (not illustrated) relative to a track or rail. The image capturing portion can be operable to rotate 360 degrees during image acquisition. The image capturing portion may rotate around a central point or axis, allowing image data of the patient to be acquired from multiple directions or in multiple planes. The scanner S can include those disclosed in U.S. Pat. Nos. 7,188,998; 7,108,421; 7,106,825; 7,001,045; and 6,940,941; all of which are incorporated herein by reference, or any appropriate portions thereof.

For a discussion of an example of a system 10 that includes EM tracking and registration methods, see, U.S. Pat. No. 8,238,631, the content of which is hereby incorporated by reference as if recited in full herein. The EM tracking system may include the STEALTHSTATION® AXI EM™ Navigation System, sold by Medtronic Navigation, Inc. having a place of business in Louisville, Colo.; or can be an EM tracking system described, for example in one or more of U.S. patent application Ser. No. 10/941,782, filed Sep. 15, 2004, and entitled "METHOD AND APPARATUS FOR SURGICAL NAVIGATION"; U.S. Pat. No. 5,913,820, entitled "Position Location System," issued Jun. 22, 1999; and U.S. Pat. No. 5,592,939, entitled "Method and System for Navigating a Catheter Probe," issued Jan. 14, 1997; all of which are incorporated by reference herein. It will be understood that the tracking system 82 may also be or include any appropriate tracking system, including a STEALTHSTATION® TREON® or S7™ tracking systems having an optical localizer, similar to the optical localizer 94, and sold by Medtronic Navigation, Inc. of Louisville, Colo. Other tracking systems include an acoustic, radiation, radar, etc. The tracking systems can be used according to generally known or described techniques in the above incorporated references.

The trajectory frame assembly 100 and cooperating components or tools may be configured for use with "asleep" or "awake" neurological (e.g., brain) surgical systems.

The reference frame 1200 can extend a distance beyond an outer surface of the platform 132 with the fiducials 1210 in a fixed geometric pattern that may extend along a common plane or at different planes and can allow for AC-PC image views. The reference frame 1200, when attached to the trajectory frame assembly 100, may be particularly suitable for "awake" brain surgical procedures to track patient movement. For "asleep" neuro surgeries, the reference frame 1200 may be attached to the trajectory frame assembly 100 and/or a head fixation frame that holds a patient's head in a stationary position (FIGS. 8A, 9A, for example) or may not be used.

The starburst connector 325 can allow for positional adjustment of the reference frame 1200 relative to the patient and/or base 110 of trajectory frame assembly 100.

In some embodiments, for "asleep" procedures, the reference frame 1200 can be attached to a head fixation frame (not shown). For "awake" procedures, the reference frame 1200 can be attached to the trajectory frame as discussed above. CT or other images can be obtained at various points during the procedure, such as at final lead implantation, for example, without requiring constant imaging during a procedure.

Although not shown, in some embodiments, one or more of the surgical tools can be configured with one or more lumens and exit ports that deliver desired cellular, biological, and/or drug therapeutics to the target area, such as the brain. The tools may also incorporate transseptal needles, biopsy and/or injection needles as well as ablation means. The lumens, where used, may receive extendable needles that may exit the probe from the distal end or from the sides, proximal, distal, or even, through the electrodes to precisely deliver cellular/biological therapeutics to the desired anatomy target. This delivery configuration may be a potential way to treat patients, where the cellular/biological therapeutics can be delivered into the desired anatomy to modify their cellular function. The cells (e.g., stem cells) may improve function.

The system 10 can include one or more tracking cameras such as CCD cameras 10*c* for tracking fiducials 1210 such as optical fiducials (e.g., reflective members) for visual feedback to a display 30, such as with respect to target anatomy. Such cameras are well known to those of skill in the art. Fiducial markers that can be located and recognized by an imaging system or other system are useful in neurosurgery and other applications. See, e.g., U.S. Pat. No. 8,073,530, the content of which is hereby incorporated by reference as if recited in full herein. The imaging system S can comprise or communicate with a CT or MRI Scanner, for example. Typical operation of an exemplary system is described in U.S. Pat. No. 8,150,494, the content of which is hereby incorporated by reference as if recited in full herein. In some embodiments, the system 10 is an optically-tracked system using a camera C/10c of a tracking or navigation system 10 (FIG. 24) that detects optical fiducials 1210, e.g., reflective patches or components such as balls or spheres (which can include some on a patient for registration) and/or on tools and/or tracker probes for tracking. The systems 10 can be configured to calculate locations of the reflective members (such as, for example, tape, patches or balls/spheres) and/or to detect a defined geometric pattern of the array of fiducials, for example. These systems 10 can be modified as described herein to have a co-registration module or a concordance review using a different trajectory calculation module that does not require registration as described herein.

Further description of optical fiducials is provided in U.S. Pat. No. 8,150,494, the content of which is hereby incorporated by reference as if recited in full herein.

In some embodiments, such as for neuro/brain surgeries, the planned intrabody trajectory, with the trajectory frame assembly 100 on the patient, can be calculated and/or confirmed in an MRI scanner, post-skull opening. That is, the planned trajectory from the non-MRI image guided system can be compared to a trajectory calculated using MRI image data after the skull is opened. The remainder of the surgical procedure can be carried out in an OR (operating room) with a camera based system, with the optical fiducials used to register the patient in the surgical space. This embodiment may reduce the time demand on MRI scanner systems, but suitable sterility conditions should be observed when changing patient venues.

The system 10 can be configured to provide workflow for a unilateral or bilateral (or even a trilateral or more) procedure. Selection of the procedure type can initiate an associated work flow progression that is presented on a display with associated patient image views.

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. More particularly, the workflow steps may be carried out in a different manner, in a different order and/or with other workflow steps or may omit some or replace some workflow steps with other steps. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A trajectory frame assembly for use with a surgical system, comprising:
    a base having a patient access aperture formed therein, wherein the base is configured to be secured to a body of a patient;
    a yoke movably mounted to the base and rotatable about a roll axis;
    a platform movably mounted to the yoke and rotatable about a pitch axis;
    a support column secured to an X-Y support table of the platform; and
    a reference bracket attached to the base under the yoke, wherein the reference bracket has an arcuate bridging arm that extends between a first connector and a second connector, at least one of which comprises a starburst connector configuration with a serrated segment and a bore.

2. The trajectory frame assembly of claim 1, wherein the arcuate bridging arm has a perimeter with opposing laterally spaced apart long sides, one at a first radius of curvature and one at a greater second radius of curvature, the first radius of curvature that is between 0.5 inches and 2 inches.

3. The trajectory frame assembly of claim 1, wherein the bridging arm positions axially extending centerlines of the first and second connectors a distance apart of between 0.5 and 3 inches, optionally between 0.5 inches and 1.5 inches.

4. The trajectory frame assembly of claim 1, wherein the support column releasably engages a mount holding a tracking probe with reflective members arranged in a fixed geometric relationship relative to each other, and wherein the reflective members are configured to be detectable by a camera-based tracking system.

5. The trajectory frame assembly of claim 1, wherein the support column releasably engages a microelectric probe driver adapter.

6. The trajectory frame assembly of claim 1, wherein the reference bracket is attached to a reference frame with a plurality of spaced apart arms comprising fiducials and/or tracking members.

* * * * *